US007521465B2

(12) United States Patent
Nag et al.

(10) Patent No.: US 7,521,465 B2
(45) Date of Patent: *Apr. 21, 2009

(54) DIPHENYL ETHER DERIVATIVES

(75) Inventors: Bishwajit Nag, Union City, CA (US);
Abhijeet Nag, Fremont, CA (US);
Debendranath Dey, Fremont, CA (US);
Shiv Kumar Agarwal, Delhi (IN);
Partha Neogi, Fremont, CA (US);
Gaddam Om Reddy, Tamil Nadu (IN);
Sangamesh Badiger, Tamil Nadu (IN);
Gajendra Singh, Tamil Nadu (IN);
Surendra Kumar Pandey, Tamil Nadu (IN); Santhanagopalan Chithra, Tamil Nadu (IN)

(73) Assignee: Bexel Pharmaceuticals, Inc., Union City, CA (US)

( * ) Notice: Subject to any disclaimer, the term of this patent is extended or adjusted under 35 U.S.C. 154(b) by 212 days.

This patent is subject to a terminal disclaimer.

(21) Appl. No.: 11/096,718

(22) Filed: Mar. 31, 2005

(65) Prior Publication Data

US 2005/0288341 A1    Dec. 29, 2005

Related U.S. Application Data

(63) Continuation-in-part of application No. 10/947,047, filed on Sep. 21, 2004, now abandoned, which is a continuation of application No. 10/356,113, filed on Jan. 31, 2003, now Pat. No. 6,794,401.

(60) Provisional application No. 60/440,772, filed on Jan. 17, 2003.

(30) Foreign Application Priority Data

Feb. 17, 2005   (IN) .......................... 347/DEL/2005

(51) Int. Cl.
*A61K 31/426* (2006.01)
*A61K 31/421* (2006.01)

(52) U.S. Cl. .................... 514/369; 514/376; 514/389; 548/227; 548/317.1

(58) Field of Classification Search ................. 514/369, 514/376; 548/183, 227, 317.1
See application file for complete search history.

(56) References Cited

U.S. PATENT DOCUMENTS

| 5,166,137 | A | 11/1992 | Otterlei et al. ................ 514/23 |
| 5,441,971 | A | 8/1995 | Sohda et al. ................ 514/342 |
| 5,527,546 | A | 6/1996 | Penza et al. ................. 424/573 |
| 6,004,813 | A | 12/1999 | Serlupi-Crescenzi et al. ........................ 435/375 |
| 6,147,100 | A | 11/2000 | Seno et al. ................. 514/369 |
| 6,316,465 | B1 | 11/2001 | Pershadsingh et al. |
| 6,331,633 | B1 | 12/2001 | Neogi et al. ................. 548/183 |
| 6,515,003 | B1 | 2/2003 | Pfahl et al. |
| 6,552,058 | B1 | 4/2003 | Sohda et al. ................ 514/376 |
| 6,562,849 | B1 | 5/2003 | Fujita et al. |
| 6,617,339 | B1 | 9/2003 | Gravestock ................ 514/340 |
| 6,620,830 | B2 | 9/2003 | Chiang |
| 6,664,281 | B1 | 12/2003 | Tajima et al. ............... 514/374 |
| 6,667,328 | B2 | 12/2003 | Yoneda et al. .............. 514/365 |
| 6,680,387 | B2 | 1/2004 | Druzgala et al. ............ 548/182 |
| 6,686,475 | B2 | 2/2004 | Hindley ..................... 548/183 |
| 6,699,896 | B1 | 3/2004 | Malamas ................... 514/374 |
| 6,706,746 | B2 | 3/2004 | Fujita et al. ................ 514/369 |
| 6,730,687 | B1 | 5/2004 | Miyachi et al. ............. 514/369 |
| 6,765,013 | B2 | 7/2004 | Pfahl et al. |
| 6,794,401 | B2 | 9/2004 | Nag et al. |
| 7,087,576 | B2 | 8/2006 | Nag et al. |
| 2003/0229120 | A1 | 12/2003 | Olsen et al. |

FOREIGN PATENT DOCUMENTS

| EP | 1 148 054 A1 | 10/2001 |
| EP | 1 213 287 A1 | 6/2002 |
| JP | 2001-308814 | 11/2001 |
| WO | WO 00/64888 | 11/2000 |
| WO | WO 01/02377 A1 | 1/2001 |
| WO | WO 03027081 | 4/2003 |
| WO | WO 2004/066964 | 8/2004 |
| WO | WO 2004080480 | 9/2004 |
| WO | WO 2006/089225 | 8/2006 |

OTHER PUBLICATIONS

International Search Report, from corresponding International Application No. PCT/US2004/00790, issued Jan. 3, 2005.
International Written Opinion, from corresponding International Application No. PCT/US2004/00790, issued Jan. 3, 2005.
International Search Report, from corresponding International Application No. PCT/US2006/005846, issued Jun. 22, 2006.
International Written Opinion, from corresponding International Application No. PCT/US2006/005846, issued Jun. 22, 2006.
International Search Report, from corresponding Internationasl Application No. PCT/US04/32931, issued Feb. 11, 2005.
International Written Opinion, from corresponding International Application No. PCT/US04/32931, issued Feb. 11, 2005.
Derivative: Definition. Accessed online on Oct. 18, 2005 at http://www.answers.com/derivative. 1 pg.
Analogue: Definition. Accessed online Oct. 18, 2005 at http;//www.answers.com/analogue. 1 pg.
Moser et al., J Clin Invest, 83:444-55,1989.
Haworth et al., Eur J Immunol, 21:2575-79, 1991.
Brennan et al., Inhibitory effect of TNFα Antibodies on Synovial Cell Interleukin-1 Production in Rheumatoid Arthritis, Lancet, vol. 334:244-7, 1989.

(Continued)

*Primary Examiner*—Kamal A Saeed
(74) *Attorney, Agent, or Firm*—Weaver Austin Villeneuve & Sampson LLP

(57) ABSTRACT

Novel diphenyl ether derivatives are provided that exhibit activity useful for reducing glucose, cholesterol, and/or triglyceride levels in plasma, and for treatment of obesity, inflammation, immunological diseases, autoimmune diseases, diabetes and disorders associated with insulin resistance.

24 Claims, 13 Drawing Sheets

OTHER PUBLICATIONS

Arend et al., Arthritis Rheum, 38:151-60,1995.
Goldenberg, Clin Ther, 21:75-87, 1999.
Luong et al., Ann Pharmacother, 34:743-60, 2000.
Georgian Office Action, dated Dec. 27, 2006, from corresponding International Application No. AP2004008942.
China Office Action, dated Oct. 20, 2006, from corresponding International Application No. 200480006737.9.
Singapore Second Written Opinion, dated Nov. 17, 2006, from corresponding International Application No. 200504369-0.
European Search Report from corresponding European Application No. 04701752.0 Issued Jun. 1, 2007.
Singapore Examination Report from corresponding Singapore Application No. 200504369-0 Issued Aug. 29, 2007.
New Zealand Examination Report dated Apr. 24, 2008 for corresponding New Zealand Application No. 541328.
Fujimoto et al., *Diabetes*, 2005, 54, 1340.

Triglyceride Level in Serum of STZ-Treated and

Cholesterol Level in STZ model

*p<0.05

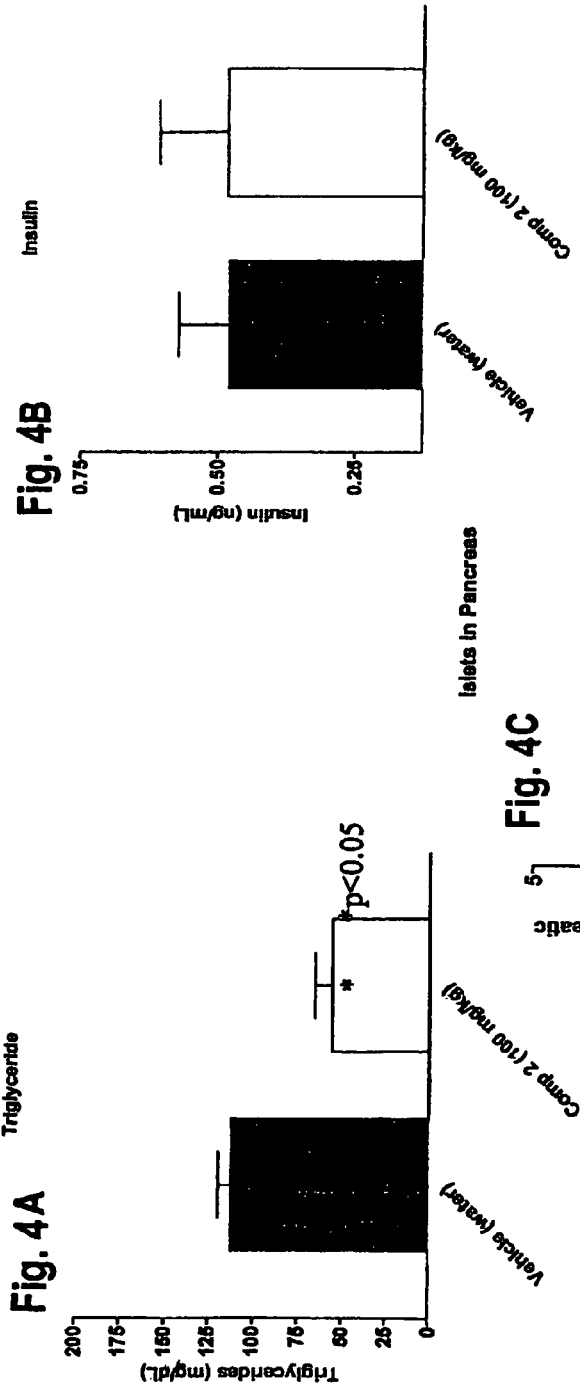
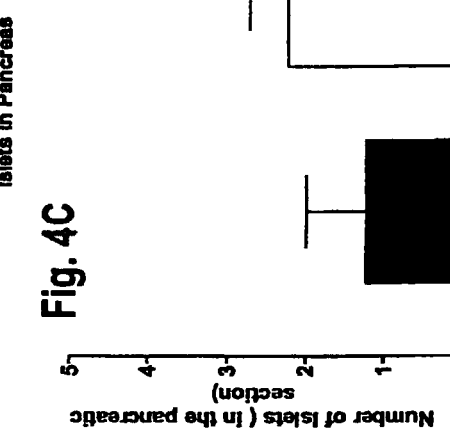
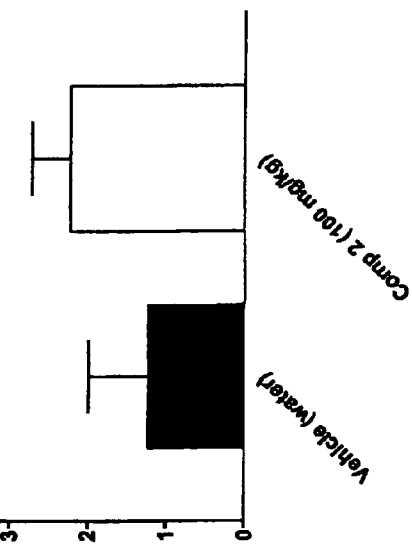
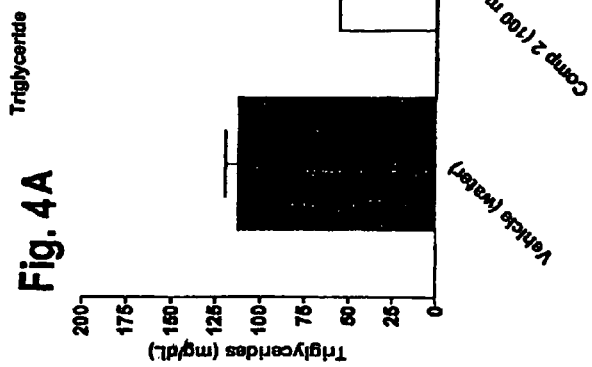

Once daily oral dose at 50 mg/kg body weight, n = 5

Once daily oral dose at 50 mg/kg body weight for 6 days

Blood Glucose Levels of ob/ob Mice

Aldose Reductase Inhibition by Comp 16

Aldose Reductase Inhibition by comp 2

DIPHENYL ETHER DERIVATIVES

RELATED APPLICATIONS

This application is a continuation-in-part of application Ser. No. 10/947,047, filed Sep. 21, 2004 now abandoned, which is a continuation of application Ser. No. 10/356,113, filed Jan. 31, 2003, now U.S. Pat. No. 6,794,401, which claims priority pursuant to 35 USC 119(e) of provisional application Ser. No. 60/440,772, filed Jan. 17, 2003, the disclosures of which are incorporated by reference herein in their entirety. Priority is also claimed pursuant to 35 USC 119 of Indian application Ser. No. 347/DEL/2005, filed Feb. 14, 2005, the disclosure of which is incorporated by reference herein in its entirety.

FIELD OF THE INVENTION

The present invention relates to novel diphenyl ether derivatives of formula (I), their analogs, their tautomeric forms, their stereoisomers, their polymorphs, their pharmaceutically acceptable salts, their pharmaceutically acceptable solvates and pharmaceutically acceptable compositions containing them.

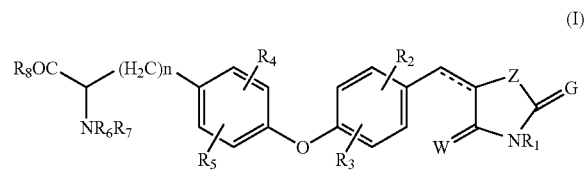

(I)

The present invention also relates to a process for the preparation of the above said novel compounds, their analogs, their derivatives, their tautomeric forms, their stereoisomers, their polymorphs, their pharmaceutically acceptable salts, pharmaceutically acceptable solvates, novel intermediates and pharmaceutical compositions containing them.

The compounds of the present invention are effective in lowering blood glucose, serum insulin, free fatty acids, cholesterol and triglyceride levels and are useful in the treatment and/or prophylaxis of type II diabetes. The compounds of the present invention are effective in treatment of obesity, inflammation, autoimmune diseases such as such as multiple sclerosis and rheumatoid arthritis. Surprisingly, these compounds increase the leptin level and have no liver toxicity.

Furthermore, the compounds of the present invention are useful for the treatment of disorders associated with insulin resistance, such as polycystic ovary syndrome, as well as hyperlipidemia, coronary artery disease and peripheral vascular disease, and for the treatment of inflammation and immunological diseases, particularly those mediated by cytokines such as TNF-α, IL-1, IL-6, IL-1β and cyclooxygenase such as COX-2. The compounds of this class are also useful for the treatment of diabetes complications like retinopathy, neuropathy, and nephropathy and like.

BACKGROUND OF THE INVENTION

The causes of type I and II diabetes are not yet clear, although both genetics and environment seem to be the factors. Type I is an autonomic immune disease and patient must take insulin to survive. Type II diabetes is more common form, is metabolic disorder resulting from the inability of the body to make a sufficient amount of insulin or to properly use the insulin that is produced. Insulin secretion and insulin resistance are considered the major defects, however, the precise genetic factors involved in the mechanism remain unknown.

Patients with diabetes usually have one or more of the following defects:
Less production of insulin by the pancreas;
Over secretion of glucose by the liver;
Independent of the glucose uptake by the skeletal muscles;
Defects in glucose transporters, desensitization of insulin receptors; and
Defects in the metabolic breakdown of polysaccharides.

Other than the parenteral or subcutaneous administration of insulin, there are about four classes of oral hypoglycemic agents used, i.e., sulfonylurea, biguanides, alpha glucosidase inhibitors and thiazolidinediones.

Each of the current agents available for use in treatment of diabetes has certain disadvantages. Accordingly, there is a continuing interest in the identification and development of new agents, which can be orally administered, for use in the treatment of diabetes.

The thiazolidinedione class listed above has gained more widespread use in recent years for treatment of type II diabetes, exhibiting particular usefulness as insulin sensitizers to combat "insulin resistance", a condition in which the patient becomes less responsive to the effects of insulin. There is a continuing need for nontoxic, more widely effective insulin sensitizers.

Recent advances in scientific understanding of the mediators involved in acute and chronic inflammatory diseases and cancer have led to new strategies in the search for effective therapeutics. Traditional approaches include direct target intervention such as the use of specific antibodies, receptor antagonists, or enzyme inhibitors. Recent breakthroughs in the elucidation of regulatory mechanisms involved in the transcription and translation of a variety of mediators have led to increased interest in therapeutic approaches directed at the level of gene transcription.

As indicated above, the present invention is also concerned with treatment of immunological diseases or inflammation, notably such diseases as are mediated by cytokines or cyclooxygenase. The principal elements of the immune system are macrophages or antigen-presenting cells, T cells and B cells. The roles of other immune cells such as NK cells, basophils, mast cells and dendritic cells are known, but their roles in primary immunologic disorders are not fully elucidated. Macrophages are important mediators of both inflammation and of processes providing the necessary "help" for T cell stimulation and proliferation. Most importantly macrophages make IL 1, IL 12 and TNF-α, all of which are potent pro-inflammatory molecules, and also provide help for T cells. In addition, activation of macrophages results in the induction of enzymes, such as cyclooxygenase II (COX-2) and inducible nitric oxide synthase (iNOS), and the production of free radicals capable of damaging normal cells. Many factors activate macrophages, including bacterial products, superantigens and interferon gamma (IFN γ). Phosphotyrosine kinases (PTKs) and other undefined cellular kinases may also be involved in the activation process.

Cytokines are molecules secreted by immune cells that are important in mediating immune responses. Cytokine production may lead to the secretion of other cytokines, altered cellular function, cell division or differentiation. Inflammation is the body's normal response to injury or infection. However, in inflammatory diseases such as rheumatoid arthritis, pathologic inflammatory processes can lead to morbidity and mortality. The cytokine tumor necrosis factoralpha (TNF-α) plays a central role in the inflammatory response and has been targeted as a point of intervention in inflammatory disease. TNF-α is a polypeptide hormone released by activated macrophages and other cells. At low concentrations, TNF-α participates in the protective inflammatory response by activating leukocytes and promoting their migration to extravascular sites of inflammation (Moser et al., J Clin Invest, 83:444-55,1989). At higher concentrations, TNF-α can act as a potent pyrogen and induce the production of other pro-inflammatory cytokines (Haworth et al., Eur J Immunol, 21:2575-79, 1991; Brennan et al., Lancet, 2:244-7, 1989). TNF-α also stimulates the synthesis of acute-phase proteins. In rheumatoid arthritis, a chronic and progressive inflammatory disease affecting about 1% of the adult U.S. population, TNF-α mediates the cytokine cascade that leads to joint damage and destruction (Arend et al., Arthritis Rheum, 38:151-60,1995). Inhibitors of TNF-α, including soluble TNF receptors (etanercept) (Goldenberg, Clin Ther, 21:75-87, 1999) and anti-TNF-α antibody (infliximab) (Luong et al., Ann Pharmacother, 34:743-60, 2000), have recently been approved by the U.S. Food and Drug Administration (FDA) as agents for the treatment of rheumatoid arthritis.

Elevated levels of TNF-α have also been implicated in many other disorders and disease conditions, including cachexia, septic shock syndrome, osteoarthritis, inflammatory bowel disease such as Crohn's disease and ulcerative colitis.

Thus it can be seen that inhibitors of TNF-α are potentially useful in the treatment of a wide variety of diseases.

While there have been prior efforts to provide compounds for inhibiting TNF-α, IL-1, IL-6, COX-2 or other agents considered responsible for immune response, inflammation or inflammatory diseases, e.g., arthritis, there still remains a need for new and improved compounds for effectively treating or inhibiting such diseases.

An object of the present invention is therefore to provide novel diphenyl ether derivatives, their analogs, their tautomeric forms, their stereoisomers, their polymorphs, their pharmaceutically acceptable salts, their pharmaceutically acceptable solvates and pharmaceutical compositions containing them, or their mixtures.

Another object of the present invention is to provide novel diphenyl ether derivatives, their analogs, their tautomeric forms, their stereoisomers, their polymorphs, their pharmaceutically acceptable salts, their pharmaceutically acceptable solvates and pharmaceutical compositions containing them or their mixtures that are useful for treatment of disorders associated with insulin resistance, such as polycystic ovary syndrome, as well as hyperlipidemia, coronary artery disease and peripheral vascular disease, and for the treatment of inflammation and immunological diseases, particularly those mediated by cytokines such as TNF-α, IL-1, IL-6, IL-1β and cyclooxygenase such as COX-2.

Another object of the present invention is to provide novel diphenyl ether derivatives, their analogs, their tautomeric forms, their stereoisomers, their polymorphs, their pharmaceutically acceptable salts, their pharmaceutically acceptable solvates and pharmaceutical compositions containing them or their mixtures having enhanced activities, without toxic effect or with reduced toxic effect.

Yet another object of the present invention is to provide a process for the preparation of novel diphenyl ether derivatives of formula (I), their analogs, their tautomeric forms, their stereoisomers, their polymorphs, their pharmaceutically acceptable salts and their pharmaceutically acceptable solvates.

SUMMARY OF THE INVENTION

The present invention, relates to novel diphenyl ether derivatives of formula (I)

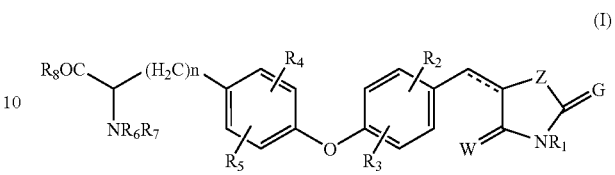

their analogs, their tautomeric forms, their stereoisomers, their polymorphs, their pharmaceutically acceptable salts, their pharmaceutically acceptable solvates, wherein ---- represents an optional bond;

W represents O or S;

Z represents $CR_{10}$, O or S;

G represents O, S or together with $R_{10}$ forms a 5 or 6 membered aromatic or heteroaromatic ring system containing 1 or 2 heteroatoms selected from O, S or N;

$R_2$, $R_3$, $R_4$ and $R_5$ are selected from hydrogen, halogen such as fluorine, chlorine, bromine or iodine; hydroxy, nitro, cyano, formyl, amino, linear or branched, substituted or unsubstituted ($C_1$-$C_6$) alkyl group such as methyl, ethyl, propyl, isopropyl, n-butyl, isobutyl, t-butyl, and the like; substituted or unsubstituted ($C_1$-$C_6$) alkoxy group such as methoxy, ethoxy, propoxy, butoxy and the like;

$R_6$ and $R_7$ may be same or different and independently represent H, $COR_{12}$, substituted or unsubstituted groups selected from alkyl, alkenyl, aryl, heteroaryl or heterocyclyl; where $R_{12}$ represents H, substituted or unsubstituted groups selected from alkyl, alkenyl, aryl, alkenyloxy, aryloxy, alkoxy, aralkyl or aralkoxy;

$R_8$ represents $—OR_{13}$ or $NR_{14}R_{15}$; where $R_{13}$ represents hydrogen, substituted or unsubstituted groups selected from alkyl, alkenyl, aryl, aralkyl, heteroaryl, or a counterion; $R_{14}$ and $R_{15}$ may be same or different and independently represent H or substituted or unsubstituted alkyl, alkenyl or aryl;

$R_1$ represents hydrogen, substituted or unsubstituted alkyl, alkenyl, $—CH_2COOR$, or aryl, or counterion; where R represents H or ($C_1$-$C_6$) alkyl;

$R_{10}$ optionally together with G forms a 5 or 6 membered aromatic or heteroaromatic ring system such as phenyl, naphthyl, furyl, pyrrolyl, pyridyl and the like.

In one class of compounds W and G represent O; Z represents S; $R_{13}$ is selected from H, substituted and unsubstituted ($C_1$-$C_6$) alkyl and a counterion; and $R_{14}$ and $R_{15}$ are independently selected from substituted and unsubstituted ($C_1$-$C_6$) alkyl. A subclass of this class includes those compounds wherein $R_2$ and $R_3$ are independently selected from H, halo, nitro, substituted and unsubstituted ($C_1$-$C_6$) alkyl and substituted and unsubstituted ($C_1$-$C_6$) alkoxy.

In another class of compounds W represents O; G and Z represent S; and $R_{13}$ is selected from substituted and unsubstituted ($C_1$-$C_6$) alkyl.

A subclass of this class includes those compounds wherein $R_2$ and $R_3$ are independently selected from H, halo, substituted and unsubstituted ($C_1$-$C_6$) alkyl and substituted and unsubstituted ($C_1$-$C_6$) alkoxy.

Yet another class of compound includes those in which the ---- is present and W represents O; G and Z represent S;

and $R_{13}$ is selected from substituted and unsubstituted ($C_1$-$C_6$) alkyl; and $R_1$ represents —$CH_2COOR$. A subclass of this class includes those compounds wherein $R_2$ and $R_3$ are independently selected from H, halo, substituted and unsubstituted ($C_1$-$C_6$) alkyl and substituted and unsubstituted ($C_1$-$C_6$) alkoxy.

Another class of compound includes those in which the ---- is absent and W represents O; G and Z represent S; and $R_{13}$ is selected from substituted and unsubstituted ($C_1$-$C_6$) alkyl; and $R_1$ represents —$CH_2COOR$. A subclass of this class includes those compounds wherein $R_2$ and $R_3$ are independently selected from H and substituted and unsubstituted ($C_1$-$C_6$) alkyl.

The invention is further directed to methods for reducing glucose, fatty acids, cholesterol and triglyceride levels in plasma comprising administering an effective amount of a compound of formula (I), their analogs, their tautomeric forms, their stereoisomers, their pharmaceutically acceptable salts, and/or their pharmaceutically acceptable solvates to a patient in need thereof.

The invention is also directed to methods for treating obesity, autoimmune diseases, inflammation, immunological diseases, diabetes and disorders associated with insulin resistance comprising administering an effective amount of a compound of formula (I), their analogs, their tautomeric forms, their stereoisomers, their pharmaceutically acceptable salts, and/or their pharmaceutically acceptable solvates to a patient in need thereof.

BRIEF DESCRIPTION OF THE FIGURES

FIGS. 4A, 4B and 4C are bar graphs showing the triglyceride and insulin levels and pancreatic islet count in mice treated with compound 2 as described in Example 50.

DETAILED DESCRIPTION OF THE INVENTION

Figure 1:
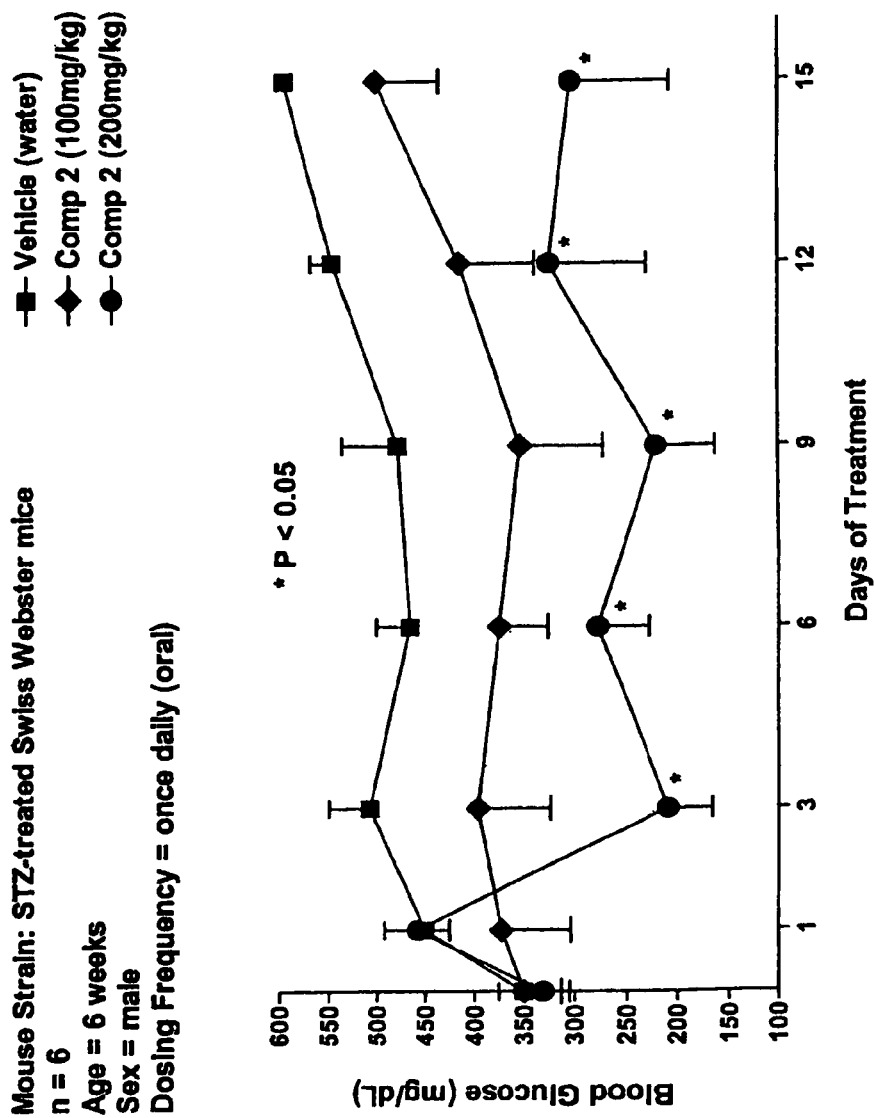
FIG. 1 is a plot of the blood glucose levels of streptozotocin-induced mice given compound 2 as described in Example 47.

In an embodiment of the present invention, the groups represented by $R_2$, $R_3$, $R_4$ and $R_5$ are selected from hydrogen, halogen such as fluorine, chlorine, bromine or iodine; hydroxy, nitro, cyano, formyl, amino, linear or branched, substituted or unsubstituted ($C_1$-$C_{20}$) alkyl group such as methyl, ethyl, propyl, isopropyl, n-butyl, isobutyl, t-butyl, pentyl, hexyl, octyl, nonyl and the like; substituted or unsubstituted ($C_1$-$C_{20}$) alkoxy group such as methoxy, ethoxy, propoxy, butoxy and the like. Alkyl and alkoxy include linear, branched and cyclic hydrocarbon structures and combinations thereof. Lower alkyl and alkoxy groups are preferred, i.e., those have 1-6 carbon atoms.

Suitable groups represented by $R_6$ and $R_7$ may be same or different and independently represent H, $COR_{12}$, substituted or unsubstituted groups selected from ($C_1$-$C_{20}$) alkyl, ($C_2$-$C_{20}$) alkenyl, ($C_5$-$C_{14}$) aryl, ($C_1$-$C_{13}$) heteroaryl; and ($C_1$-$C_{11}$) heterocyclyl. Aryl or heteroaryl groups include a 4, 5 or 6 membered ring system containing 0 (aryl) or 1-4 heteroatoms (heteroaryl) selected from O, N and S; a 9 or 10-membered bicyclic ring system containing 0 (aryl) or 1 or more heteroatoms (heteroaryl); or a 12 to 14-membered tricyclic ring system containing 0 (aryl) or 1 or more heteroatoms (heteroaryl). The group $R_{12}$ represents H, substituted or unsubstituted ($C_1$-$C_{20}$) alkyl, ($C_2$-$C_{20}$) alkenyl, ($C_5$-$C_{14}$) aryl, ($C_2$-$C_{20}$) alkenyloxy, ($C_5$-$C_{14}$) aryloxy, ($C_1$-$C_{20}$) alkoxy, or ($C_6$-$C_{34}$) aralkoxy.

Suitable groups represented by $R_1$ are selected from hydrogen, substituted or unsubstituted ($C_1$-$C_{20}$) alkyl, ($C_2$-$C_{20}$) alkenyl, $CH_2COOR$, ($C_5$-$C_{14}$) aryl or a counterion.

Suitable groups represented by $R_{13}$ are selected from hydrogen, substituted or unsubstituted ($C_1$-$C_{20}$) alkyl, preferably lower alkyl such as methyl, ethyl, n-propyl, isopropyl, n-butyl, isobutyl, t-butyl; ($C_2$-$C_{20}$) alkenyl; ($C_5$-$C_{14}$) aryl such as phenyl; ($C_6$-$C_{34}$) aralkyl group such as benzyl; ($C_1$-$C_{13}$) heteroaryl; a counter ion selected from alkali metal like Li, Na, and K; alkaline earth metal like Ca and Mg; salts of different bases such as ammonium or substituted ammonium salts, diethanolamine, α-phenylethylamine, benzylamine, piperidine, morpholine, pyridine, hydroxyethylpyrrolidine, hydroxyethylpiperidine, choline and the like, aluminum, tromethamine and the like.

Suitable groups represented by $R_{14}$ and $R_{15}$ are selected from hydrogen, substituted or unsubstituted ($C_1$-$C_{20}$) alkyl group, preferably lower alkyl such as methyl, ethyl, n-propyl, isopropyl, n-butyl, isobutyl, t-butyl and the like; ($C_2$-$C_{20}$) alkenyl; and ($C_5$-$C_{14}$) aryl such as phenyl.

One class of compounds of the formula I includes those in which the ---- is present or absent and W and G represent O; Z represents S; $R_{13}$ is selected from H, substituted and unsubstituted ($C_1$-$C_6$) alkyl and a counterion; and $R_{14}$ and $R_{15}$ are independently selected from substituted and unsubstituted ($C_1$-$C_6$) alkyl. A subclass of this class includes those compounds wherein $R_2$ and $R_3$ are independently selected from H, halo, nitro, substituted and unsubstituted ($C_1$-$C_6$) alkyl and substituted and unsubstituted ($C_1$-$C_6$) alkoxy.

Another class of compounds of the Formula I includes those in which the ---- is present or absent and W represents O; G and Z represent S; and $R_{13}$ is selected from substituted and unsubstituted ($C_1$-$C_6$) alkyl. A subclass of this class includes those compounds wherein $R_2$ and $R_3$ are independently selected from H, halo, substituted and unsubstituted ($C_1$-$C_6$) alkyl and substituted and unsubstituted ($C_1$-$C_6$) alkoxy.

Yet another class of compounds of the Formula I includes those in which the ---- is present and W represents O; G and Z represent S; and $R_{13}$ is selected from substituted and unsubstituted ($C_1$-$C_6$) alkyl; and $R_1$ represents —$CH_2COOR$. A subclass of this class includes those compounds wherein $R_2$ and $R_3$ are independently selected from H, halo, substituted and unsubstituted ($C_1$-$C_6$) alkyl and substituted and unsubstituted ($C_1$-$C_6$) alkoxy.

Another class of compounds of the Formula I includes those in which the ---- is absent and W represents O; G and Z represent S; and $R_{13}$ is selected from substituted and unsubstituted ($C_1$-$C_6$) alkyl; and R, represents —$CH_2COOR$. A subclass of this class includes those compounds wherein $R_2$ and $R_3$ are independently selected from H and substituted and unsubstituted ($C_1$-$C_6$) alkyl.

The term analog includes a compound which differs from the parent structure by one or more C, N, O or S atoms. Hence, a compound in which one of the N atoms in the parent structure is replaced by an S atom, the latter compound is an analog of the former.

The term stereoisomer includes isomers that differ from one another in the way the atoms are arranged in space, but whose chemical formulas and structures are otherwise identical. Stereoisomers include enantiomers and diastereoisomers.

The term tautomers includes readily interconvertible isomeric forms of a compound in equilibrium. The enol-keto tautomerism is an example.

The term polymorphs includes crystallographically distinct forms of compounds with chemically identical structures.

The term pharmaceutically acceptable solvates includes combinations of solvent molecules with molecules or ions of the solute compound.

The term substituted means that one or more hydrogen atoms are replaced by a substituent including, but not limited to, alkyl, alkoxy, alkylenedioxy, amino, amidino, aryl, aralkyl (e.g., benzyl), aryloxy (e.g., phenoxy), aralkoxy (e.g., benzyloxy), carboalkoxy (e.g., acyloxy), carboxyalkyl (e.g., esters), carboxamido, aminocarbonyl, cyano, carbonyl, halo, hydroxyl, heteroaryl, heteroaralkyl, heteroaryloxy, heteroaralkoxy, nitro, sulfanyl, sulfinyl, sulfonyl, and thio. In addition, the substituent may be substituted.

Pharmaceutically acceptable salts forming part of this invention include base addition salts such as alkali metal salts like Li, Na, and K salts, alkaline earth metal salts like Ca and Mg salts, salts of organic bases such as lysine, arginine, guanidine, diethanolamine, choline and the like, ammonium or substituted ammonium salts. Salts may include acid addition salts which are sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, ketoglutarates and the like. Pharmaceutically acceptable solvates may be hydrates or comprising other solvents of crystallization such as alcohols.

Particularly useful compounds according to the invention include:

(S)-2-Amino-3-{4-[4-(2,4-dioxo-thiazolidin-5-ylidenemethyl)-phenoxy]-phenyl}-propionic acid methyl ester hydrochloric acid salt (S)-2-Amino-3-{4-[4-(2,4-dioxo-thiazolidin-5-ylmethyl)-phenoxy]-phenyl}-propionic acid methyl ester hydrochloric acid salt (S)-2-Amino-3-{4-[4-(2,4-dioxo-thiazolidin-5-ylidenemethyl)-3-fluoro-phenoxy]-phenyl}-propionic acid methyl ester hydrochloric acid salt (S)-2-Amino-3-{4-[2-chloro-4-(2,4-dioxo-thiazolidin-5-ylidenemethyl)-phenoxy]-phenyl}-propionic acid methyl ester hydrochloric acid salt (S)-2-Amino-3-{4-[3-chloro-4-(2,4-dioxo-thiazolidin-5-ylidenemethyl)-phenoxy]-phenyl}-propionic acid methyl ester hydrochloric acid salt (S)-2-Amino-3-{4-[4-(2,4-dioxo-thiazolidin-5-ylidenemethyl)-2-methoxy-phenoxy]-phenyl}-propionic acid methyl ester hydrochloric acid salt (S)-2-Amino-3-{4-[4-(2,4-dioxo-thiazolidin-5-ylidenemethyl)-2-nitro-phenoxy]-phenyl}-propionic acid methyl ester hydrochloric acid salt (S)-2-Amino-3-{4-[4-(2,4-dioxo-thiazolidin-5-ylidenemethyl)-3-trifluoromethyl-phenoxy]-phenyl}-propionic acid methyl ester hydrochloric acid salt (S)-2-Amino-3-{4-[4-(2,4-dioxo-thiazolidin-5-ylidenemethyl)-phenoxy]-phenyl}-propionic acid (S)-2-Amino-3-{4-[4-(2,4-dioxo-thiazolidin-5-ylidenemethyl)-phenoxy]-phenyl}-propionate dipotassium salt (S)-2-Amino-3-{4-[4-(2,4-dioxo-thiazolidin-5-ylidenemethyl)-phenoxy]-phenyl}-propionate disodium salt (S)-2-Amino-3-{4-[3-chloro-4-(2,4-dioxo-thiazolidin-5-ylmethyl)-phenoxy]-phenyl}-propionic acid methyl ester hydrochloric acid salt (S)-2-Amino-3-{4-[2-chloro-4-(2,4-dioxo-thiazolidin-5-ylmethyl)-phenoxy]-phenyl}-propionic acid methyl ester hydrochloric acid salt (S)-2-Amino-3-{4-[4-(2,4-dioxo-thiazolidin-5-ylmethyl)-2-methoxy-phenoxy]-phenyl}-propionic acid methyl ester hydrochloric acid salt (S)-2-Amino-3-{4-[4-(2,4-dioxo-thiazolidin-5-ylmethyl)-2-fluoro-phenoxy]-phenyl}-propionic acid methyl ester hydrochloric acid salt (S)-2-Amino-3-{4-[4-(2,4-dioxo-thiazolidin-5-ylmethyl)-phenoxy]-phenyl}-propionic acid hydrochloric acid salt (COMPOUND 16)

(S)-2-Amino-3-{4-[4-(2,4-dioxo-thiazolidin-5-ylmethyl)-phenoxy]-phenyl}-propionate disodium salt (S)-2-Amino-3-{4-[4-(2,4-dioxo-thiazolidin-5-ylmethyl)-phenoxy]-phenyl}-propionate dipotassium salt (S)-2-Amino-3-{4-[4-(2,4-dioxo-thiazolidin-5-ylmethyl)-phenoxy]-phenyl}-N,N-dimethyl-propionamide hydrochloric acid salt (R,S)-2-Amino-3-{4-[4-(4-oxo-2-thioxo-thiazolidin-5-ylidenemethyl)-phenoxy]-phenyl}-propionic acid methyl ester hydrochloric acid salt (COMPOUND 20)

(S)-2-Amino-3-{4-[3-fluoro-4-(4-oxo-2-thioxo-thiazolidin-5-ylidenemethyl)-phenoxy]-phenyl}-propionic acid methyl ester hydrochloric acid salt (S)-2-Amino-3-{4-[2-fluoro-4-(4-oxo-2-thioxo-thiazolidin-5-ylidenemethyl)-phenoxy]-phenyl}-propionic acid methyl ester hydrochloric acid salt (S)-2-Amino-3-{4-[3-chloro-4-(4-oxo-2-thioxo-thiazolidin-5-ylidenemethyl)-phenoxy]-phenyl}-propionic acid methyl ester hydrochloric acid salt (S)-2-Amino-3-{4-[2-chloro-4-(4-oxo-2-thioxo-thiazolidin-5-ylidenemethyl)-phenoxy]-phenyl}-propionic acid methyl ester hydrochloric acid salt (S)-2-Amino-3-{4-[2-methoxy-4-(4-oxo-2-thioxo-thiazolidin-5-ylidenemethyl)-phenoxy]-phenyl}-propionic acid methyl ester hydrochloric acid salt (S)-2-Amino-3-{4-[4-(4-oxo-2-thioxo-thiazolidin-5-ylidenemethyl)-phenoxy]-phenyl}-propionic acid methyl ester (S)-2-Amino-3-{4-[4-(4-oxo-2-thioxo-thiazolidin-5-ylidenemethyl)-2-trifluoromethyl-phenoxy]-phenyl}-propionic acid methyl ester hydrochloric acid salt (S)-2-Amino-3-{4-[4-(4-oxo-2-thioxo-thiazolidin-5-ylidenemethyl)-3-trifluoromethyl-phenoxy]-phenyl}-propionic acid methyl ester hydrochloric acid salt (S)-2-Amino-3-{4-[2-methoxy-4-(4-oxo-2-thioxo-thiazolidin-5-ylmethyl)-phenoxy]-phenyl}-propionic acid methyl ester hydrochloric acid salt (R,S)-2-Amino-3-{4-[4-(4-oxo-2-thioxo-thiazolidin-5-ylmethyl)-phenoxy]-phenyl}-propionic acid methyl ester (S)-2-Amino-3-{4-[2-chloro-4-(4-oxo-2-thioxo-thiazolidin-5-ylmethyl)-phenoxy]-phenyl}-propionic acid methyl ester hydrochloric acid salt (S)-2-Amino-3-{4-[3-chloro-4-(4-oxo-2-thioxo-thiazolidin-5-ylmethyl)-phenoxy]-phenyl}-propionic acid methyl ester hydrochloric acid salt (S)-2-Amino-3-{4-[3-fluoro-4-(4-oxo-2-thioxo-thiazolidin-5-ylmethyl)-phenoxy]-phenyl}-propionic acid methyl ester hydrochloric acid salt (S)-2-Amino-3-{4-[2-fluoro-4-(4-oxo-2-thioxo-thiazolidin-5-ylmethyl)-phenoxy]-phenyl}-propionic acid methyl ester hydrochloric acid salt (S)-2-Amino-3-{4-[4-(4-oxo-2-thioxo-thiazolidin-5-ylmethyl)-3-trifluoromethyl-phenoxy]-phenyl}-propionic acid methyl ester hydrochloric acid salt (R,S)-2-Amino-3-{4-[4-(3-carboxymethyl-4-oxo-2-thioxo-thiazolidin-5-ylidenemethyl)-phenoxy]-phenyl}-propionic acid methyl ester hydrochloric acid salt (COMPOUND 36)

(S)-2-Amino-3-{4-[4-(3-carboxymethyl-4-oxo-2-thioxo-thiazolidin-5-ylidenemethyl)-3-chloro-phenoxy]-phenyl}-propionic acid methyl ester hydrochloric acid salt (S)-2-Amino-3-{4-[4-(3-carboxymethyl-4-oxo-2-thioxo-thiazolidin-5-ylidenemethyl)-2-chloro-phenoxy]-phenyl}-propionic acid methyl ester hydrochloric acid salt (S)-2-Amino-3-{4-[4-(3-carboxymethyl-4-oxo-2-thioxo-thiazolidin-5-ylidenemethyl)-2-fluoro-phenoxy]-phenyl}-propionic acid methyl ester hydrochloric acid salt (S)-2-Amino-3-{4-[4-(3-carboxymethyl-4-oxo-2-thioxo-thiazolidin-5-ylidenemethyl)-2-trifluoromethyl-phenoxy]-phenyl}-propionic acid methyl ester hydrochloric acid salt (S)-2-Amino-3-{4-[4-(3-carboxymethyl-4-oxo-2-thioxo-thiazolidin-5-ylidenemethyl)-3-fluoro-phenoxy]-phenyl}-propionic acid methyl ester hydrochloric acid salt (S)-2-Amino-3-{4-[4-(3-carboxymethyl-4-oxo-2-thioxo-thiazolidin-5-ylidenemethyl)-3-trifluoromethyl-phenoxy]-phenyl}-propionic acid methyl ester hydrochloric acid salt (S)-2-Amino-3-{4-[4-(3-carboxymethyl-4-oxo-2-thioxo-thiazolidin-5-ylidenemethyl)-2-methoxy-phenoxy]-phenyl}-propionic acid methyl ester hydrochloric acid salt (R,S)-2-Amino-3-{4-[4-(3-carboxymethyl-4-oxo-2-thioxo-thiazolidin-5-ylmethyl)-phenoxy]-phenyl}-propionic acid methyl ester hydrochloric acid salt (S)-2-Amino-3-{4-[4-(3-carboxymethyl-4-oxo-2-thioxo-thiazolidin-5-ylmethyl)-phenoxy]-phenyl}-propionic acid methyl ester hydrochloric acid salt (S)-2-Amino-3-{4-[4-(3-carboxymethyl-4-oxo-2-thioxo-thiazolidin-5-ylmethyl)-3-trifluoromethyl-phenoxy]-phenyl}-propionic acid methyl ester hydrochloric acid salt Preferred salts for the list of compounds above are hydrochloride, hydrobromide, sodium, potassium or magnesium.

Structures of compounds within the scope of the invention and their glucose uptake in 3T3L-1 cells are provided in the following Tables I-IV:

TABLE I

Table I reference formula

| Cmpd No. | $R_1$ | $R_2$ | X | Y | Z | Glucose uptake in 3T3L-1 cells (1 µM) |
|---|---|---|---|---|---|---|
| 10 | H | H | K | none | K | 2.07 |
| 11 | H | H | Na | none | Na | 1.49 |
| 3 | F | H | $CH_3$ | HCl | H | 1.20 |
| 5 | Cl | H | $CH_3$ | HCl | H | NC |
| 6 | H | $OCH_3$ | $CH_3$ | HCl | H | NC |
| 7 | H | $NO_2$ | $CH_3$ | HCl | H | NC |

NC = less than 1.2 fold above basal

TABLE II

Table II reference formula

| Cmpd No. | $R_1$ | $R_2$ | X | Y | Z | Glucose uptake in 3T3L-1 cells (1 µM) |
|---|---|---|---|---|---|---|
| 2 S-isomer | H | H | $CH_3$ | HCl | H | 1.79 |
| 2 R-isomer | H | H | $CH_3$ | HCl | H | 1.68 |
| 16 | H | H | H | HCl | H | 1.69* |
| 19 | H | H | $N(CH_3)_2$ | HCl | H | 1.82 |
| 12 | Cl | H | $CH_3$ | HCl | H | 1.45 |
| 13 | H | Cl | $CH_3$ | HCl | H | 1.61 |

TABLE III

Table III reference formula

| Cmpd No. | R₁ | R₂ | Glucose uptake in 3T3L-1 cell (1 μM) |
|---|---|---|---|
| 20 | H | H | NC |
| 21 | F | H | NC |
| 22 | H | F | NC |
| 23 | Cl | H | NC |
| 24 | H | Cl | 1.39 |

NC = less than 1.2 fold above basal

TABLE IV

Table IV reference formula

| Cmpd No. | R₁ | R₂ | Glucose uptake in 3T3L-1 cells (1 μM) |
|---|---|---|---|
| 37 | Cl | H | NC |
| 38 | H | Cl | 1.59 |
| 40 | H | CF₃ | 1.54 |

NC = less than 1.2 fold above basal

According to another feature of the present invention, there is provided a process for the preparation of compounds of formula (I), wherein ---- represents a bond and all other symbols are as defined earlier, as shown in scheme-I

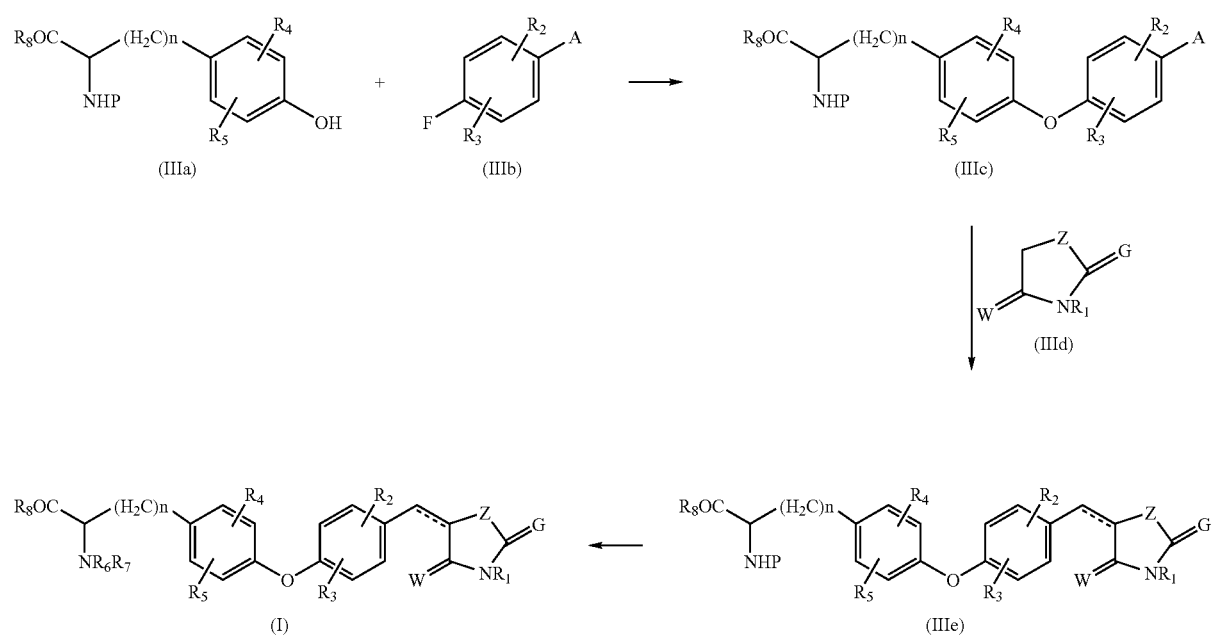

Scheme-I wherein;

A=CHO or $CH_2$-M; P is an N-protecting group;

---- may or may not represent a bond;

M represents a suitable leaving group selected from chloro, bromo, iodo, $OSO_2CH_3$, O—$SO_2$Ph, O—$SO_2C_6H_4$—$CH_3$ and similar leaving groups.

The reaction of compound of formula (IIIa) with the compound of formula (IIIb produce a compound of formula (IIIc) in the presence of solvents such as THF, DMF, DMSO, DME and the like or mixtures of solvents may be used. The reaction may be carried out in an inert atmosphere. The reaction may be effected in the presence of a base such as $K_2CO_3$, $Na_2CO_3$, NaH or mixtures thereof. The reaction temperature may range from 20° C. to 150° C., preferably at a temperature in the range of 30° C. to 100° C. The duration of the reaction may range from 1 to 24 hours, preferably from 2 to 6 hours. The reaction of the compound of the general formula (IIIc) with a compound of formula (IIId) may be carried out by following ways:

a. by making C—C bond with the reaction of aldehyde group and active methylene group of (IIId) by affecting the dehydration;

b. by making C—N bond when A is $CH_2M$ group and attched to ring nitrogen of (IIId) in the presence of base.

Both approaches can be carried out in the presence of base and in the presence of a solvent such as toluene, methoxyethanol or mixtures thereof to yield a compound of formula (IIIe). The reaction temperature may range from 60° C. to 180° C., when the reaction is carried out neat in the presence of sodium acetate. Suitable catalyst such as piperidinium acetate or benzoate, sodium acetate or mixtures of catalysts may also be employed. Sodium acetate can be used in the presence of solvent, but it is preferred that sodium acetate is used neat. The water produced in the reaction may be removed by using Dean Stark water separator or by using water-absorbing agents like molecular sieves.

The deprotection of formula (IIIe) to yield compound of formula (I) may be carried out using acids such as HCl, sulfuric acid, acetic acid in the presence of solvents such as DCM, ethyl acetate, water and the like or mixture thereof at a temperature in the range of −10° C. to 50° C.

In another embodiment of the present invention, there is provided a process for the preparation of compounds of formula (I), by reducing the penultimate step of formula (I) wherein ---- represents bond. The reduction step is not required when ---- represent no bond and all other symbols are as defined earlier. The reduction may be carried out in the presence of gaseous hydrogen and a catalyst such as Pd/C, Rh/C, Pt/C, Raney Nickel, and the like. Mixtures of catalysts may be used. The reaction may be conducted in the presence of solvents such as methanol, dichloromethane, dioxane, acetic acid, ethyl acetate and the like. Mixtures of solvents may be used. A pressure between atmospheric pressure to 100 psi may be employed. The catalyst may be 5-10% Pd/C and the amount of catalyst used may range from 50-300% w/w.

The protecting group P used in the invention are conventional protecting groups such as t-butoxy carbonyl (t-Boc), trityl, trifluoroacetyl, benzyloxy, benzyloxy carbonyl (Cbz) and the like.

The pharmaceutically acceptable salts are prepared by reacting the compound of formula (I) with 1 to 4 equivalents of a base such as sodium hydroxide, sodium methoxide, sodium hydride, potassium t-butoxide, calcium hydroxide, magnesium hydroxide and the like, in solvents like ether, THF, methanol, t-butanol, dioxane, isopropanol, ethanol etc. Mixtures of solvents may be used. Organic bases like lysine, arginine, diethanolamine, choline, guanidine and their derivatives etc. may also be used. Alternatively, acid addition salts are prepared by treatment with acids such as hydrochloric acid, hydrobromic acid, nitric acid, sulfuric acid, phosphoric acid, p-toluenesulfonic acid, methanesulfonic acid, acetic acid, citric acid, maleic acid, salicylic acid, hydroxynaphthoic acid, ascorbic acid, palmitic acid, succinic acid, benzoic acid, benzene sulfonic acid, tartaric acid and the like in solvents like ethyl acetate, ether, alcohols, acetone, THF, dioxane etc. Mixture of solvents may also be used.

The present invention also provides a pharmaceutical composition, containing one or more of the compounds of the general formula (I) as defined above, their tautomeric forms, their derivatives, their analogues, their stereoisomers, their polymorphs, their pharmaceutically acceptable salts, their pharmaceutically acceptable solvates in combination with the usual pharmaceutically employed carriers, diluents and the like.

The pharmaceutical composition may be in the forms normally employed, such as tablets, capsules, powders, syrups, solutions, suspensions and the like, may contain flavorants, sweeteners etc. in suitable solid or liquid carriers or diluents, or in suitable sterile media to form injectable solutions or suspensions. Such compositions typically contain from 1 to 25%, preferably 1 to 15% by weight of active compound, the remainder of the composition being pharmaceutically acceptable carriers, diluents, excipients or solvents.

Suitable pharmaceutically acceptable carriers include solid fillers or diluents and sterile aqueous or organic solutions. The active compound will be present in such pharmaceutical compositions in the amounts sufficient to provide the desired dosage in the range as described above. Thus, for oral administration, the compounds can be combined with a suitable solid or liquid carrier or diluent to form capsules, tablets, powders, syrups, solutions, suspensions and the like. The pharmaceutical compositions, may, if desired, contain additional components such as flavorants, sweeteners, excipients and the like. For parenteral administration, the compounds can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable acid addition salts or alkali or alkaline earth metal salts of the compounds. The injectable solutions prepared in this manner can then be, administered intravenously, intraperitoneally, subcutaneously, or intramuscularly, with intramuscular administration being preferred in humans.

The pharmaceutical compositions of the invention are effective in lowering blood glucose, serum insulin and triglyceride levels, as shown by tests in animal models of diabetes. The pharmaceutical compositions of the invention are thus effective for treating diabetes, Type I or Type II. The pharmaceutical compositions of the invention are also effective in the treatment of obesity, inflammation, autoimmune diseases. The pharmaceutical compositions of the present invention are also effective in lowering free fatty acid and cholesterol levels in plasma. Furthermore, pharmaceutical compositions of the present invention are useful for the treatment of disorders associated with insulin resistance, such as polycystic ovary syndrome, as well as hyperlipidemia, coronary artery disease and peripheral vascular disease, and for the treatment of inflammation and immunological diseases, particularly those mediated by cytokines such as TNF-α, IL-1, IL-6 and cyclooxygenase such as COX-2. Generally, the effective dose for treating a particular condition in a patient may be readily determined and adjusted by the physician during treatment to alleviate the symptoms or indications of the condition or disease. Generally, a daily dose of active compound in the range of about 0.01 to 1000 mg/kg of body weight is appropriate for administration to obtain effective results. The daily dose may be administered in a single dose or divided into several doses. In some cases, depending upon the individual response, it may be necessary to deviate upwards or downwards from the initially prescribed daily dose. Typical pharmaceutical preparations normally contain from about 0.2 to about 500 mg of active compound of formula I and/or its pharmaceutically active salts or solvates per dose.

The term "therapeutically effective amount" or "effective amount" refers to that amount of a compound or mixture of compounds of Formula I that is sufficient to effect treatment, as defined below, when administered alone or in combination with other therapies to a mammal in need of such treatment. More specifically, it is that amount that is sufficient to lower the plasma levels of glucose, fatty acids, cholesterol or triglycerides or to treat obesity, autoimmune diseases, inflammation, immunological diseases, diabetes and disorders associated with insulin resistance. The term "animal" as used herein is meant to include all mammals, and in particular humans. Such animals are also referred to herein as subjects or patients in need of treatment. The therapeutically effective amount will vary depending upon the subject and disease condition being treated, the weight and age of the subject, the severity of the disease condition, the particular compound of Formula I chosen, the dosing regimen to be followed, timing of administration, the manner of administration and the like, all of which can readily be determined by one of ordinary skill in the art.

The term "treatment" or "treating" means any treatment of a disease in a mammal, including:

a) preventing the disease, that is, causing the clinical symptoms of the disease not to develop;

b) inhibiting the disease, that is, slowing or arresting the development of clinical symptoms; and/or c) relieving the disease, that is, causing the regression of clinical symptoms.

The invention is explained in detail in the examples given below which are provided by way of illustration only and therefore should not be construed to limit the scope of the invention.

EXAMPLE 1

Synthesis of 5-[4-(4-(2-amino-2-methoxycarbonylethyl)phenoxy)benzilidene]-thiazolidin-2,4-dione Hydrochloride Salt

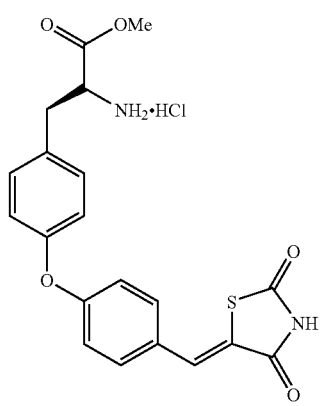

(1)

Step I: Preparation of (S)-2-tert-Butoxycarbonylamino-3-(4-(4-formylphenoxy)phenyl)-propanoic acid

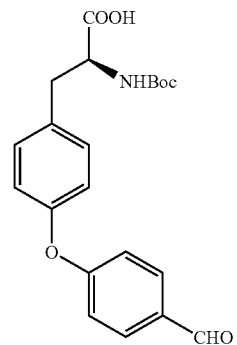

Dissolve N-tert-butoxycarbonyl-L-tyrosine (2.42 Kg, 8.3 moles) in dry DMF (7.26 L) under argon and still till complete dissolution. Add $K_2CO_3$ (3.57 Kg, 25.81 moles), 4-fluorobenzaldeyde (5.34 Kg, 43.01 moles) and stir at 70±5° C. for 48 h under argon. Cool the reaction mixture less than 30° C. Poured the reaction mixture in water (75 L) and stir for 15 min. Add ethyl acetate (40 L) and stir for 30 min. Separate the organic layer and aqueous layer was acidified with HCl (6M) to pH 2. Solid precipitated was dissolved in ethyl acetate (40 L) and aqueous layer was separated. Organic layer was washed with brine (40 L), dried on sodium sulfate and evaporate solvent under reduced pressure. Observed HPLC purity (93.4%) and chiral purity by HPLC (100%). Dry with anhydrous $MgSO_4$ and evaporate under reduced pressure. Pale yellow solid (3.06 Kg, 99.3%). $^1$H NMR (300 MHz, DMSO-$d_6$): 9.89 (s, 1H), 7.82 (d, J=8.4 Hz, 2H), 7.23 (d, J=8.4 Hz, 2H), 7.00 (overlapped d, J=9.0 Hz, 4H), 4.63 (m, 1H), 3.2 (m, 1H), 3.06 (m, 1H), 1.40 (s, 9H).

Step II: Preparation of (S)-2-tert-Butoxycarbonylamino-3-(4-(4-formylphenoxy)phenyl)-propanoic acid methyl ester

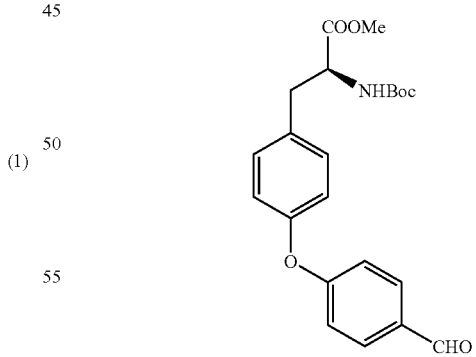

Dissolve (S)-2-tert-butoxycarbonylamino-3-(4-(4-formylphenoxy)phenyl)-propanoic acid (2.97 Kg, 7.7 moles) in dry DMF (14.84 L). Add $NaHCO_3$ (1.29 Kg, 15.4 moles) and iodomethane (6.56 Kg, 46.19 moles) under inert atmosphere and stirred at room temperature for 14 h. Check completion of the reaction by TLC ($SiO_2$ gel, $CHCl_3$-MeOH, 9:1). Poured the reaction mixture in water and stirred for 15 min. Add ethyl acetate (40 L). Oraganic layer was washed with brine and evaporated under reduced pressure. Yield 3.06 Kg, 99.3%, HPLC purity 94.6% and chiral purity 100% ee. $^1$HNMR (300 MHz, CDCl$_3$): 9.92 (s, 1H), 7.83 (d, J=8.7 Hz, 2H), 7.16 (d, J=8.7 Hz, 2H), 7.02 (overlapped d, 4H), 5.03 (brs, 1H), 4.59 (m, 1H), 3.74 (s, 3H), 3.13 (dd, J=5.7 and 13.8 Hz, 1H), 3.00 (dd, J=6.3 and 13.8 Hz, 1H), 1.43 (3, 9H).

Step III: Preparation of (S)-2-tert-Butoxycarbonylamino-3-{4-[4-(2,4-dioxothiazolidin-5-ylidenemethyl)-phenoxy]-phenyl}-propionic acid methyl ester

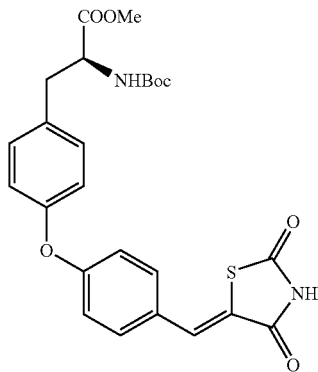

Dissolve (S)-2-tert-butoxycarbonylamino-3-(4-(4-formylphenoxy)phenyl)-propanoic acid methyl ester (3.05 Kg, 7.64 moles) in toluene (18 L). Add benzoic acid (144.9 g), piperidine (87.6 g) and 2,4-thiazolidinedione (1.11 Kg, 20.5) sequentially. Remove water azeotropically for 6 h. Check completion of the reaction by TLC (SiO$_2$ gel, CHCl$_3$-MeOH, 19:1). Distil off half of the solvent and cool down to room temperature, washed with 5% sodium bicarbonate solution, water, brine and dried over anhydrous sodium sulfate. Yield 3.80 Kg, 99.9%, chiral purity 100% ee. $^1$HNMR (300 MHz, CD$_3$OD): 7.75 (s, 1H), 7.52 (d, J=9.0 Hz, 2H) 7.26 (d, J=8.4 Hz, 2H), 7.26 (d, J=8.4 Hz, 2H), 7.03 (d, J=9.0 Hz, 2H), 6.95 (d, J=9.0 Hz, 2H), 4.38 (m, 1H), 3.71 (S, 3H), 3.12 (dd, J=5.4 and 13.5 Hz, 1H), 2.85 (dd, J=9.3 and 13.5 Hz, 1H), 1.30 (s, 9H).

Step IV: Preparation 5-[4-(4-(2-amino-2-methoxycarbonylethyl) phenoxy)benzilidene]thiazolidin-2,4-dione hydrochloride salt

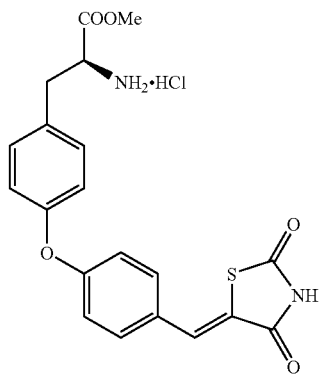

(1)

Dry HCl gas was passed slowly to the solution of 2-tert-butoxycarbonylamino-3-{4-[4-(2-oxo-1,2-dihydro-indol-3-ylidenemethyl)-phenoxy]-phenyl}-propionic acid methyl ester (1.2 g, 2.4 mmol) in dichloromethane (100 ml) at 0° C. to 5° C. for 2 hr. After completion of the reaction, the excess of hydrochloric acid gas was removed by bubbling nitrogen gas. The solid thus separated out was filtered, washed with dichloromethane (25 ml) and dried to furnish the titled product (0.84 g, 80.56%), $^1$H NMR (D$_2$O, 400 MHz) δppm: 7.76(s, 1H), 7.62(d, 2H), 7.30(d, 2H), 7.1(m, 4H), 4.3(t, 1H), 3.73(s, 3H), 3.14(m, 2H), m/z$^{M+1}$ 399.2.

EXAMPLE 2

Synthesis of (S)-2-Amino-3-{4-[4-(2,4-dioxothiazolidin-5-ylmethyl)-phenoxy]-phenyl}-propionic acid methyl ester hydrochloride (COMPOUND 2)

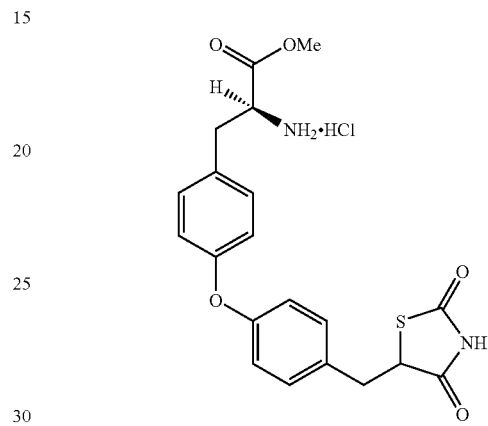

Step I: Preparation of (S)-2-Amino-3-{4-[4-(2,4-dioxothiazolidin-5-ylidenemethyl)-phenoxy]-phenyl}-propionic acid methyl ester hydrochloride

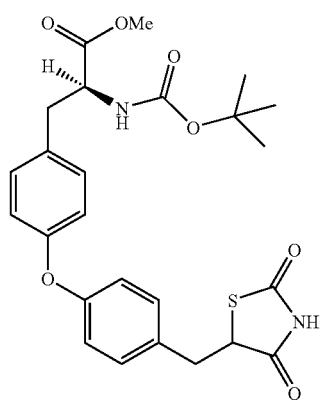

Dissolve (S)-2-tert-butoxycarbonylamino-3-{4-[4-(2,4-dioxothiazolidin-5-ylidenemethyl)-phenoxy]-phenyl}-propionic acid methyl ester (2.5 Kg, 5.02 moles) in methanol (25 L). Under nitrogen atmosphere add palladium on charcoal (10%, 940 g, wet 50%). Raised temperature to 75±5° C. and charged hydrogen at 150-200 psi and maintained for 18 h. Completion of the reaction monitored by HPLC. Cooled to room temperature and filter the catalyst through a bed of Celite®. Wash the bed with methanol. Evaporate solvent and dry the compound. Yield 100%, 2.51 Kg. $^1$HNMR (300 MHz, CDCl$_3$); 7.18 (d, J=8.7 Hz, 2H), 7.10 (d, J=8.7 Hz, 2H), 6.93 (overlapped d, 4H), 5.03 (br, 1H), 4.58 (m, 1H), 4.51 (dd, J=3.9 and 9.3H, 1H), 3.73 (s, 3H), 3.50 (dd, J=3.9 and 14.1 Hz, 1H), 3.13 (dd, J=9.6 and 14.1 Hz, 1H), 2.97-3.04 (m, 2H), 1.42 (s, 9H).

Step II: Preparation of (S)-2-Amino-3-{4-[4-(2,4-dioxothiazolidin-5-ylmethyl)-phenoxy]-phenyl}-propionic acid methyl ester hydrochloride

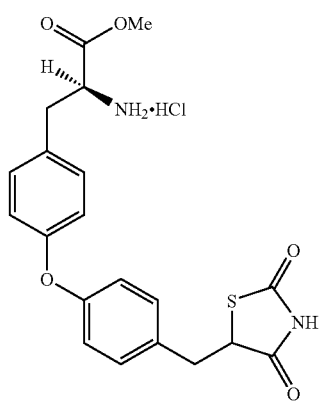

(2) Suspend Step 4 product (2.5 Kg) in MTBE (9.66 L) and methanol (9.85 L) mixture to this add 2M HCl in ether (13.6 L) and stirred the reaction mixture till reaction is complete. Purification of the crude mixture yielded 1.3 kg (60.0%) of 98.35 pure product. $^1$HNMR (300 MHz, DMSOd$_6$): 7.28 (d, J=8.7 Hz, 4H), 6.96 (overlapped d, 4.H), 4.91 (dd, J=4.2 and 9.0 Hz, 1H), 4.26 (t, J=6.9 Hz, 1H), 3.70 (s, 3H), 3.37 (dd, J=4.5 and 14.4 Hz, 1H), 3.09-3.16 (m, 2H).

EXAMPLES 3 THROUGH 11

Further compounds were prepared generally following the procedure of Example 1.

Analyses of the Compounds are Shown in Table 1.

TABLE 1

Non-reduced Thiazolidinedione Compounds

| Example No. | Structure | Analytical Data |
|---|---|---|
| 3 | (structure with COOMe, NH$_2$·HCl, F-substituted thiazolidinedione) | Yield: 0.200gm(83.3% $^1$HNMR (DMSO-d$_6$ 400MHz): δ 3.1(d, 2H), 3.7(s, 3H), 4.3(m, 1H), 6.9(m, 1 H), 7.1(m, 2H), 7.3(m, 2H), 7.5(m, 1H), 7.7(s, 1H), 8.5(bs, 2H); m/z$^{m+1}$: 417.1 |
| 4 | (structure with COOMe, NH$_2$·HCl, Cl-substituted thiazolidinedione) | Yield: 0.45gm(93.7% $^1$HNMR DMSO-d$_6$ 400MHz): δ 3.1(d, 2H), 3.7(s, 3H), 4.3(m, 1H). 7.0 (m, 3H), 7.3(d, 2H), 7.5(m, 1H), 7.8(s, 1H), 7.9(s, 1H), 8.4(bs, 2H); m/z$^{m+1}$: 433.2. |

TABLE 1-continued

Non-reduced Thiazolidinedione Compounds

| Example No. | Structure | Analytical Data |
| --- | --- | --- |
| 5 | 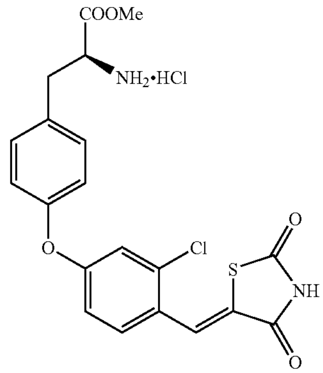 | Yield: 0.39gm(97.5%, $^1$HNMR (DMSO-$d_6$ 400MHz): δ 3.1(d, 2H), 3.7(s, 3H), 4.3(m, 1H). 7.1(m, 4H), 7.2(d, 2H), 7.5(d, 1H), 7.8(s, 1H), 8.4(bs, 2H); m/z$^{m+1}$: 433.2. |
| 6 | 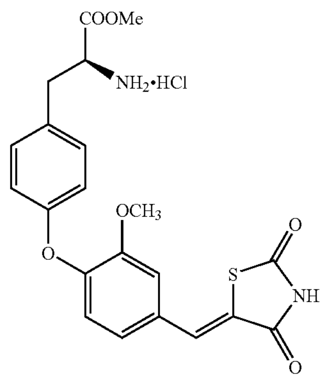 | Yield: 0.095gm(56.78%, $^1$HNMR DMSO-$d_6$ 400MHz): δ 3.1(dd, 2H), 3.71(s, 3H), 3.82(s, 3H), 4.27(t, 1H), 6.90(d, 2H), 7.00(d, 1H), 7.20(m, 3H), 7.39(d, 1H) 7.80(s, 1H) 8.4(bs, 2H); m/z$^{m+1}$: 429, |
| 7 | 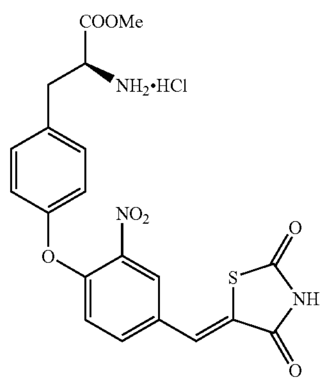 | Yield: 0.085gm(60.16%, $^1$HNMR DMSO-$d_6$ 400MHz): δ 3.16(d, 2H), 3.72(s, 3H), 4.34(t, 1H), 7.15(dd, 3H), 7.35(d, 2H), 7.86(m, 2H), 8.34(d, 1H), 8.55(bs, 2H) m/z$^{m+1}$: 444. |
| 8 | 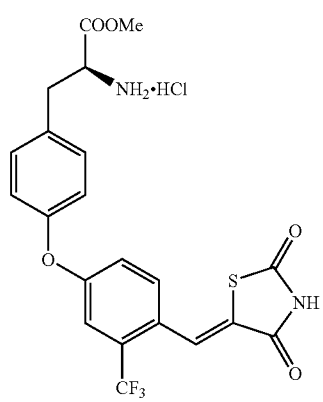 | Yield 0.131g(40.8%, HPLC Purity 91.8%); $^1$HNMR (DMSO-$d_6$ 400MHz); δ 3.1(m, 2H), 3.7(s, 3H), 4.3(m, 1H), 7.1(d, 2H), 7.3(m, 3H), 7.4 (d, 1H), 7.72(d, 1H), 7.79(s, 1H) m/z$^{m+1}$; 467.1 |

TABLE 1-continued
Non-reduced Thiazolidinedione Compounds
| Example No. | Structure | Analytical Data |
|---|---|---|
| 9 | 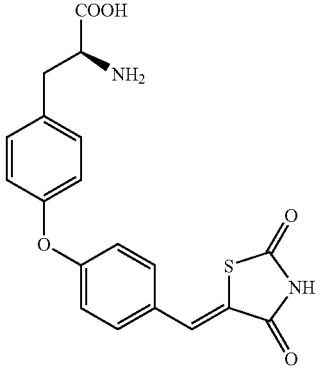 | Yield: 0.24gm(87.3%), $^1$HNMR DMSO-$d_6$ 400MHz) : δ 3.1(m, 2H), 4.2(m, 1H), 7.1(m, 4H), 7.3(d, 2H), 7.6(d, 2H), 7.7(s, 1H). m/z$^{m+1}$: 384.8, |
| 10 | 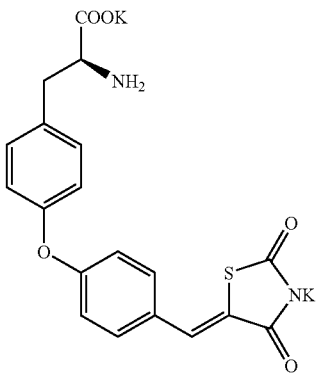 | Yield: 0.75g(82.46%), $^1$HNMR (DMSO-$d_6$, 400MHz): δ 2.4(m, 1H), 2.98(d, 1H), 3.10(m, 1H), 6.93(d, 2H), 7.03(d, 2H), 7.26 (d, 2H), 7.28(s, 1H), 7.50(d, 2H), m/z$^{m+1}$: 385.1 |
| 11 | 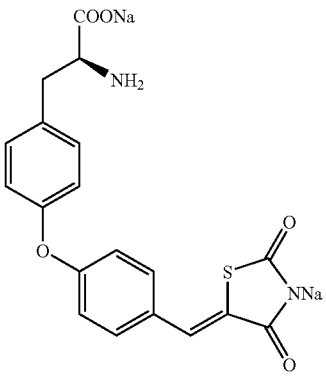 | Yield: 0.76gm(85.29%, $^1$HNMR DMSO-$d_6$ 400MHz): δ 2.4(m, 1H), 2.98(d, 1H), 3.09(m 1H), 6.93(d, 2H), 7.03(d, 2H), 7.26(d, 2H), 7.28(s, 1H), 7.50(d, 2H), m/z$^{m+1}$: 385.0 |

EXAMPLES 12 THROUGH 18

Further compounds were made generally following the procedure of Example 2.

Analyses of the Compounds are Shown in Table 2.

TABLE 2

Reduced thiazolidinedione compounds

| Example No. | Structure | Analytical Data |
|---|---|---|
| 12 | 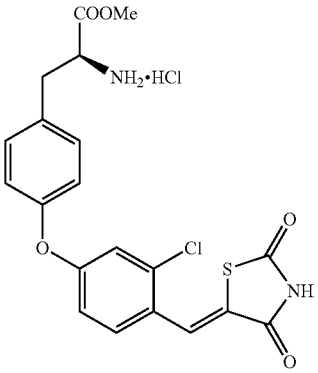 | Yield: 0.145gm(96.0%), $^1$HNMR DMSO-$d_6$ 400MHz): δ 3.0(m, 2H), 3.19(m, 1H), 3.5(m, 1H), 3.7(s, 3H), 4.2(m, 1H), 4.88(m, 1H), 6.9(m, 1H), 7.0(m, 3H), 7.2(m, 2H), 7.37(d, 1H), m/z$^{m+1}$: 435.2. |
| 13 | 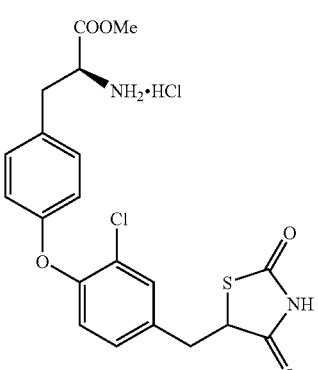 | Yield: 0.18gm(96.0%), $^1$HNMR DMSO-$d_6$ 400MHz): δ 3.02(m, 1H), 3.35(m, 1H), 3.7(s, 3H), 4.28(m, 1H), 4.95(m, 1H), 6.9(m, 2H), 7.0(d, 1H), 7.2(m, 3H), 7.5(s, 1H), m/z$^{m+1}$: 434.9. |
| 14 | 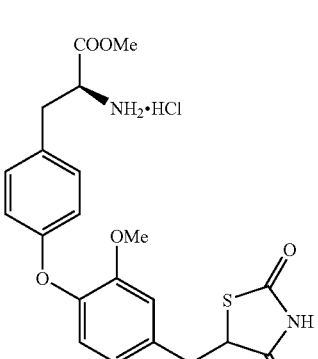 | Yield 0.180g(69.50%, HPLC Purity 94.7%); $^1$HNMR(DMSO-$d_6$ 400MHz); δ 3.1(m, 3H), 3.4(dd, 1H), 3.7(s, 3H), 3.72(s, 3H), 4.2(t, 1H), 4.9(m, 1H), 6.7(d, 2H), 6.8(d, 1H), 6.9(d, 1H), 7.0(s, 1H), 7.1(d, 2H), 8.5(bs, 2H); m/z$^{m+1}$; 431.2 |

TABLE 2-continued
Reduced thiazolidinedione compounds
| Example No. | Structure | Analytical Data |
|---|---|---|
| 15 | 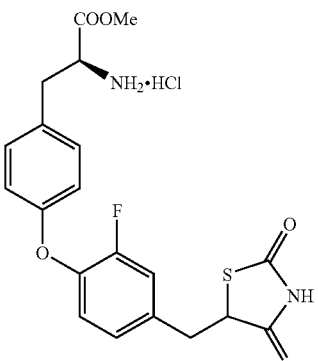 | Yield 0.49g(97.6%); ¹HNMR (DMSO-$d_6$ 400MHz); δ 3.0(m, 2H), 3.1(m, 1H), 3.4(s, 1H), 3.7(1, 3H), 4.2(m, 1H), 4.9(m, 1H), 6.9(d, 2H), 7.0(d, 2H), 7.2(d, 2H), 7.3(d, 2H); m/z$^{m+1}$; 419.1 |
| 16 | 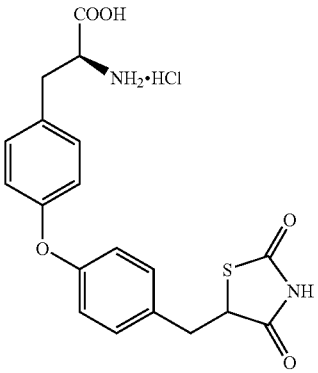 | Yield 2.8gm(93.3%, ¹HNMR DMSO-$d_6$ 400MHz): δ 3.1(m, 3H), 3.3(m, 1H), 4.1(m, 1H), 4.8(m, 1H), 6.9(m, 4H), 7.2(m, 4H). m/z$^{m+1}$: 387.1, MP-181-190° C. |
| 17 | 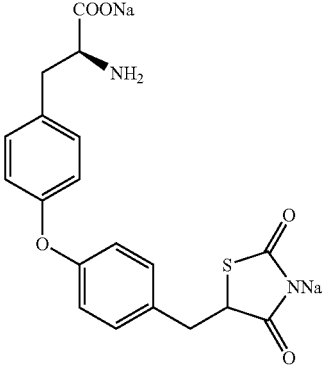 | Yield 0.620g(69.58%, HPLC Purity 98.4%); ¹HNMR(DMSO$d_6$ 400MHz); δ 2.6(m, 2H), 3.0(dd, 1H), 3.1(m, 1H), 3.4(dd, 1H), 4.2(dd, 1H), 6.8(d, 4H), 7.2(d, 4H); m/z$^{m+1}$; 387.1 |
| 18 | 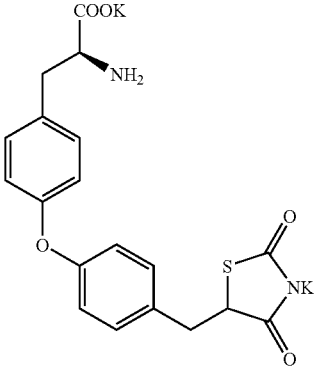 | Yield 0.600g(62.69%, HPLC Purity 90.5%); ¹HNMR(DMSO-$d_6$ 400MHz); δ 2.6(m, 2H),3.0(dd, 1H), 3.1(m, 1H), 3.3(dd, 1H), 4.2(dd, 1H), 6.8(d, 4H), 7.2(d, 4H); m/z$^{m+1}$; 387.1 |

EXAMPLE 19

Synthesis of 2-amino-3-{4-[4-(2,4-dioxothiazolidin-5-ylmethyl)-phenoxy]-phenyl}-N,N-dimethylpropionamide hydrochloric acid salt. (19)

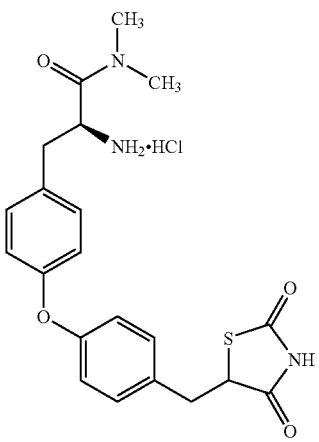

(19)

Step I

Preparation of (1-dimethylcarbamoyl-2-{4-[4-(2,4-dioxothiazolidin-5-ylmethyl)-phenoxy]-phenyl}-ethyl)-carbamic acid tert-butyl ester

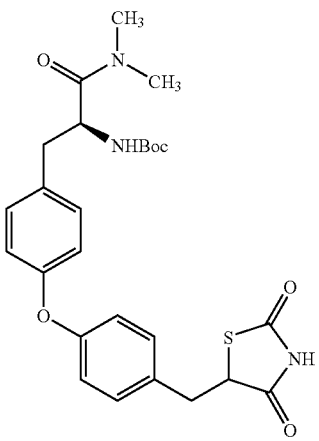

The compound, 2-tert-butoxycarbonylamino-3-{4-[4-(2, 4-dioxothiazolidin-5-ylmethyl)-phenoxy]-phenyl}-propionic acid (4.2 g, 8.63 mmol) was dissolved in $CH_2Cl_2$ (30 mL) and stirred at room temperature under an atmosphere of argon. Triethylamine (1.44 mL, 0.014 mmol) and benzotriazol-1-yloxy-tris(dimethylamino)phosphonium hexafluorophosphate (BOP reagent, 4.19 g, 9.5 mmol) were added and the reaction mixture was stirred for 15 min. Dimethylamine (2.0 M solution in THF, 5.6 mL, 11.2 mmol) was added and the resulting solution was stirred at room temperature for about 1 h. The solvent was removed under reduced pressure and the resulting oil was taken up in EtOAc (100 mL). The organic layer was extracted with 0.5 N NaOH (1×50 mL), water (1×100 mL) and brine (1×100 mL). Silica gel chromatography of the crude product with $CHCl_3$-MeOH (19:1) yielded pure amide, (1-dimethylcarbamoyl-2-{4-[4-(2,4-dioxothiazolidin-5-ylmethyl)-phenoxy]-phenyl}-ethyl)-carbamic acid tert-butyl ester (0.61 g, 13.8%). $^1$H NMR (400 MHz, $CDCl_3$): 7.17 (overlapped d, J=8.4 Hz, 2H), 7.16 (overlapped d, J=8.4 Hz, 2H), 6.92 (overlapped d, J=8.4 Hz, 2H), 6.90 (overlapped d, J=8.4 Hz, 2H), 5.51 (d, J=8.4 Hz, 1H), 4.81 (m, 1H), 3.02-3.13 (m, 2H), 2.83-2.95 (m, 5H), 2.76 (s, 3H), 1.46 (s, 9H).

Step II

Preparation of 2-amino-3-{4-[4-(2,4-dioxothiazolidin-5-ylmethyl)-phenoxy]-phenyl}-N,N-dimethylpropionamide hydrochloric acid salt

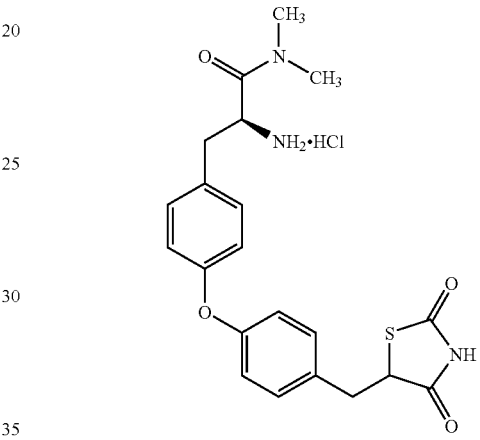

(19)

(1-dimethylcarbamoyl-2-{4-[4-(2,4-dioxothiazolidin-5-ylmethyl)-phenoxy]-phenyl}-ethyl)-carbamic acid tert-butyl ester (0.25 g) was dissolved in $CH_2Cl_2$ and cooled to 0-5° C. Hydrogen chloride gas was bubbled through this solution for 30 min. The excess HCl was degassed and the $CH_2Cl_2$ was removed. The residual solid was triturated with EtOAc (2×25 mL), decanted, and dried to yield the desired compound 2-amino-3-{4-[4-(2,4-dioxothiazolidin-5-ylmethyl)-phenoxy]-phenyl}-N,N-dimethylpropionamide hydrochloric acid salt as a white amorphous solid (0.16 g, 73.1%). $^1$H NMR (DMSO-$d_6$): 12.05 (br, 1H), 7.26 (d, J=8.4 Hz, 2H), 7.22 (d, J=8.4 Hz, 2H), 6.96 (d, J=8.4 Hz, 2H), 6.91 (d, J=8.4 Hz, 2H), 4.90 (dd, J=9.6 and 4.4 Hz, 1H), 4.53 (br, 1H), 2.91-3.14 (m, 4H), 2.81 (s, 3H), 3.05 (s, 3H).

Rhodanina and rhodanine acetic acid compounds are made by following general methods reported in Example 1 and 2 using rhodanine or rhodanine acetic acid in step III respectively. Reduction of the double for rho danine series of molecules are done by general method A and for rhodanine acetic acid series by general method B.

General Method A

To the solution of starting material (1.0 g, 1 eq) in toluene (120 ml) was added 1,4-dihydro-3,5-dicarbethoxy-2,6-dimethylpyridine (1.3 eq) and silica gel (3.0 g). The reaction mixture was heated to 80° C. and stirred for 36 hr. The progress of reaction was monitored by HPLC. Reaction mixture was filtered washed with ethyl acetate. Solvent was evaporated under reduced pressure residue was dissolve in ethyl acetate washed with dil HCl. The ethyl acetate was evaporated under reduced pressure.

General Method B

Pt(IV)oxide (0.35 mmol) was added to the solution of compound (2.62 mmol) in methanol (250 ml) and charged to hydrogenator flask. The reaction mixture was hydrogenated at 210 psi pressure for 80 hr and monitored by HPLC. The obtained crude product containing unreacted starting material was used in the next step without further purification.

EXAMPLES 20 THROUGH 46

Further compounds were prepared generally following the procedures in Example 19. Analyses of the compounds are shown in Tables 3 through 6.

TABLE 3

Non-reduced Rhodanine compounds

| Example No. | Structure | Analytical Data |
|---|---|---|
| 20 | 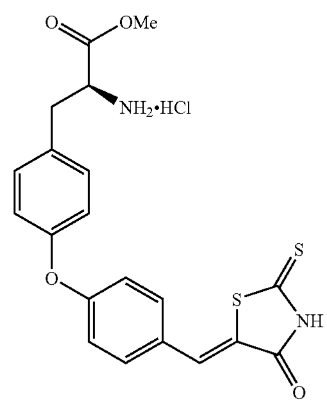 | Yield: 3.6g, (93.2%), $^1$HNMR (DMSO-$d_6$, 400MHz) δ ppm: 2.5(m, 2H), 3.7(s, 3H), 4.3(m, 1H), 7.1(q, 4H), 7.3(d, 2H), 7.6(m, 3H), 8.5(bs, 2H), m/z$^{M+1}$ 415. |
| 21 | 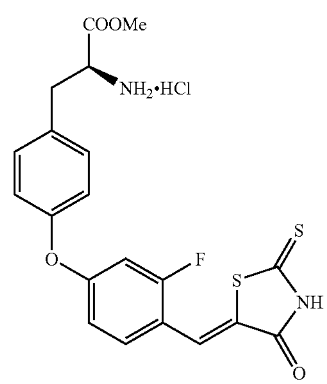 | Yield: 0.108g(69.0%), $^1$HNMR DMSO-$d_6$ 400MHz): δ 3.14(d, 2H), 3.7(s, 3H), 4.3(m, 1H), 6.98(d, 1H), 7.1(m, 3H), 7.3(m, 2H), 7.55(m, 1H), 7.7(s, 1H) m/z$^{m+1}$: 433.2. |
| 22 | 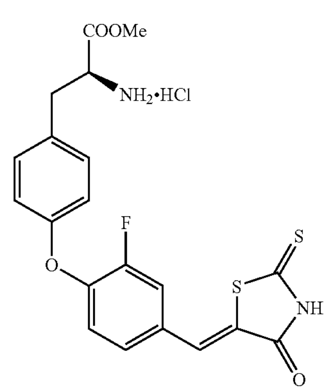 | Yield: 0.11gm(69.0%, $^1$HNMR DMSO-$d_6$ 400MHz): δ 3.1(d, 2H), 3.7(s, 3H), 4.2(m, 1H), 7.07(d, 2H), 7.09(m, 1H), 7.28(m, 2H), 7.3(m, 1H), 7.64(s, 1H), 7.75(d, 1H) m/z$^{m+1}$: 433.2. |

TABLE 3-continued

Non-reduced Rhodanine compounds

| Example No. | Structure | Analytical Data |
|---|---|---|
| 23 | 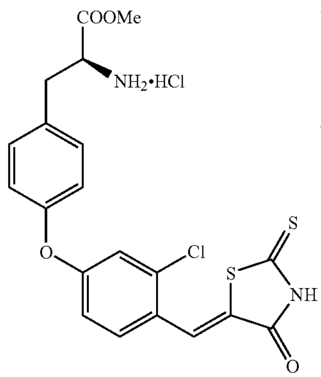 | Yield: 0.30gm(94.0%, $^1$HNMR DMSO-$d_6$ 400MHz): δ 3.0(d, 2H), 3.7(s, 3H), 4.3(m, 1H), 7.15(m, 1H), 7.17(m, 2H), 7.2(d, 1H), 7.3(d, 2H), 7.5(d, 1H), 7.7(s, 1H) m/z$^{m+1}$: 449.1. |
| 24 | 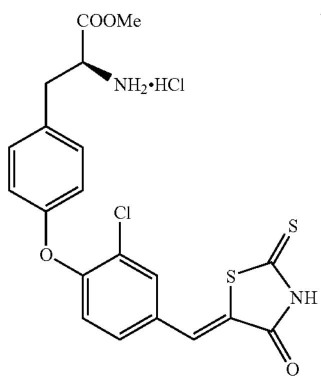 | Yield: 0.3gm(84.0%, $^1$HNMR DMSO-$d_6$ 400MHz): δ 3.12(m, 2H), 3.7(s, 3H), 4.3(m, 1H), 7.0(m, 3H), 7.3(m, 2H), 7.5(m, 1H), 7.6(s, 1H), 7.9(s, 1H), m/z$^{m+1}$: 449.1. |
| 25 | 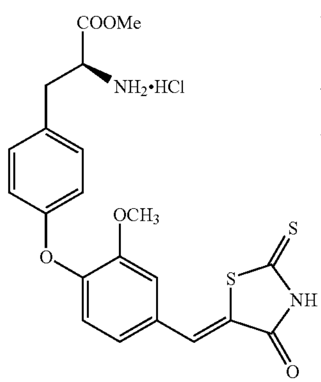 | Yield 0.125g(80.64%, HPLC Purity 93.8%); $^1$HNMR(DMSO-$d_6$ 400MHz); δ 3.1(m, 2H), 3.7(s, 3H), 3.84(s, 3H), 4.2(m, 1H), 6.9(d, 2H), 7.0(d, 1H), 7.2(m, 3H), 7.4(d, 1H), 7.6(s, 1H), 8.5(bs, 2H); m/z$^{m+1}$; 445.1 |
| 26 | 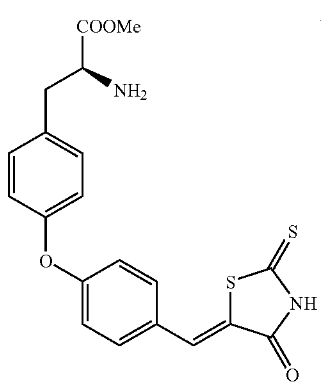 | Yield: 1.52gm(94.4%, $^1$HNMR DMSO-$d_6$ 400MHz): δ 3.1(m, 2H), 3.7(s, 3H), 4.3(m, 1H), 7.1(m, 4H), 7.3(m, 2H), 7.6(m, 3H). m/z$^{m+1}$: 414.8. |

TABLE 3-continued

Non-reduced Rhodanine compounds

| Example No. | Structure | Analytical Data |
|---|---|---|
| 27 | 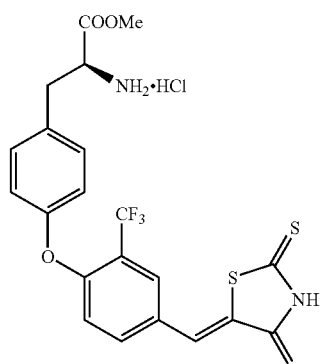 | Yield: 0.19gm(77%), $^1$HNMR DMSO-$d_6$ 400MHz): δ 3.1(d, 2H), 3.7(s, 3H), 4.3(m, 1H), 7.0(d, 1H), 7.1(d, 2H), 7.3(d, 2H)7.7(s, 1H), 7.8(s, 1H), 8.0(d, 1H), 8.5(bs, 2H); m/z$^{m+1}$; 483.0 |
| 28 | 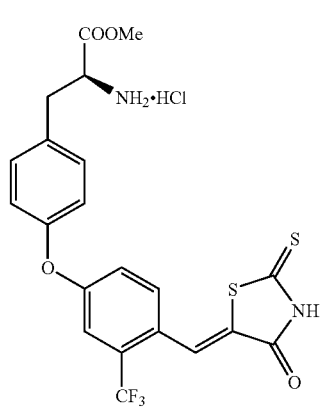 | Yield: 0.20gm(81%), $^1$HNMR DMSO-$d_6$ 400MHz): δ 3.1(m, 2H), 3.7(s, 3H), 4.3(m, 1H), 7.1(d, 2H), 7.3(m, 3H), 7.4(d, 1H)7.6(d, 1H), 7.7(d, 1H), m/z$^{m+1}$; 483.1 |

TABLE 4

Reduced Rhodanine compounds

| Example No. | Structure | Analytical Data |
|---|---|---|
| 29 | 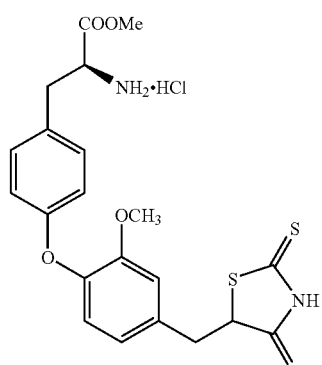 | Yield 0.139g(84.27%, HPLC Purity 95.5%); $^1$HNMR(DMSO-$d_6$ 400MHz); δ 3.0(d, 2H), 3.2(m, 1H), 3.69(s,3H), 3.72(s, 3H) 4.2(m, 1H), 5.0(m, 1H), 6.7(d, 2H), 6.8(d, 1H), 6.9(d, 1H), 7.08(s, 1H), 7.15(d, 2H), 8.4(bs, 2H); m/z$^{m+1}$; 446 |

TABLE 4-continued

Reduced Rhodanine compounds

| Example No. | Structure | Analytical Data |
|---|---|---|
| 30 | (structure) | Yield: 0.35gm(86.8%), $^1$HNMR DMSO-d$_6$ 400MHz): δ 3.1(dd, 2H), 3.7(s, 3H), 4.2(t, 1H), 5.0(t, 1H), 6.9 (m, 4H), 7.2(m, 4H), 8.5(bs, 2H), 13.1(bs, 1H).m/z$^{m+1}$: 417.1, |
| 31 | (structure) | Yield: 0.14gm(70%), $^1$HNMR DMSO-d$_6$ 400MHz): δ 3.0(m, 2H), 3.2(m, 1H), 3.3(m, 1H), 3.7(s, 3H), 4.3(m, 1H), 5.0(m, 1H), 6.8(d, 2H), 6.9(d, 2H), 7.2(m, 3H), 7.5(s, 1H), 8.41(bs, 2H).m/z$^{m+1}$: 451.1, |
| 32 | (structure) | Yield: 0.14gm(70%), $^1$HNMR DMSO-d$_6$ 400MHz): δ 3.0(m, 2H), 3.2(m, 1H), 3.3(m, 1H), 3.7(s, 3H), 4.3(m, 1H), 5.0(m, 1H), 6.9(m, 1H), 7.0(m, 3H), 7.2(m, 2H), 7.3(d,1H), 8.5(bs ,2H).m/z$^{m+1}$: 451.1, |
| 33 | (structure) | Yield: 0.090g(58.4%), $^1$HNMR DMSO-d$_6$ 400MHz): δ 3.18(m, 2H), 3.2(m, 1H), 3.38(m, 1H), 3.7(s, 3H), 4.3(m, 1H), 4.9(m, 1H), 6.8(m, 2H), 7.2(m, 2H), 7.3(m, 3H), 8.4(bs, 2H), m/z$^{m+1}$: 435.2 |

TABLE 4-continued
Reduced Rhodanine compounds
| Example No. | Structure | Analytical Data |
|---|---|---|
| 34 | 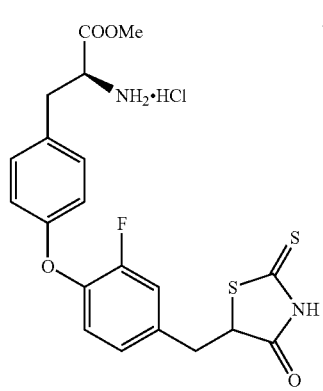 | Yield 0.100g(58.8%), ¹HNMR DMSO-d₆ 400MHz): δ 3.0(m, 2H), 3.3(m, 2H), 3.7(s, 3H), 4.2(t, 1H), 5.0(t, 1H), 6.9(d, 2H), 7.1(d, 2H), 7.29(m, 3H), 8.5(bs, 2H), m/z$^{m+1}$: 435.4 |
| 35 | 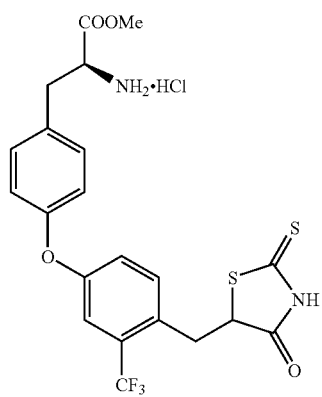 | Yield: 0.237g(77.4%), ¹HNMR DMSO-d₆ 400MHz): δ 3.12(d, 2H), 3.32(m, 1H), 3.55(m, 1H), 3.68(s, 3H), 4.30(t, 1H), 4.97(t, 1H), 7.08(d, 2H), 7.28(m, 4H), 7.53(d, 1H), m/z$^{m+1}$: 485.2 |
TABLE 5
Non-reduced Rhodanine acetic acid compounds
| Example No. | Structure | Analytical Data |
|---|---|---|
| 36 | 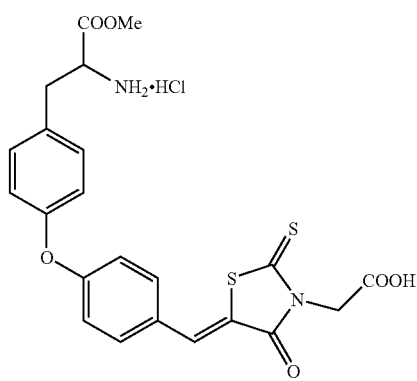 | Yield: 3.8g(92.6%), ¹HNMR (DMSO-d₆, 400MHz) δ ppm: 3.1 (2H, d), 3.7(3H, s), 4.3(1H, m), 4.7 (2H, s), 7.1(4H, m), 7.3(2H, d), 7.7(2H, d), 7.9(1H, s), 8.5(2H, bs) m/z$^{M+1}$: 473.1 |

TABLE 5-continued

Non-reduced Rhodanine acetic acid compounds

| Example No. | Structure | Analytical Data |
|---|---|---|
| 37 | 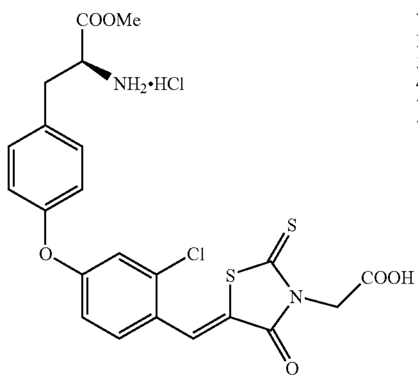 | Yield: 0.38gm(93.0%), $^1$HNMR DMSO-$d_6$ 400MHz): δ 3.0(d, 2H), 3.7(s, 3H), 4.2(m, 1H), 4.7(s, 2H), 7.1 d, 1H), 7.2(m, 2H), 7.24(s, 1H), 7.34(m, 2H), 7.63(2, 1H), 7.93(s, 1H) m/z$^{m+1}$: 507.1. |
| 38 | 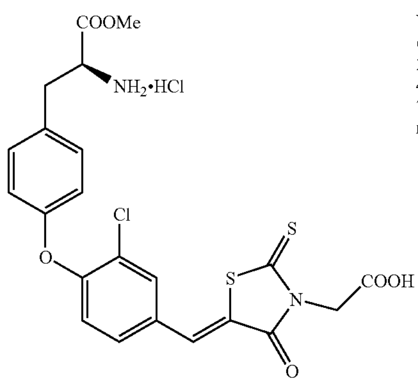 | Yield: 0.31gm(94.0%), $^1$HNMR (DMSO-$d_6$ 400MHz): δ 3.12(m, 2H), 3.7(s, 3H), 4.33(t, 1H), 4.7(s, 2H), 7.0(m, 3H), 7.3(m, 2H), 7.6(m, 1H), 7.9(s, 1H), 7.99(s, 1H), m/z$^{m+1}$: 507.1. |
| 39 | 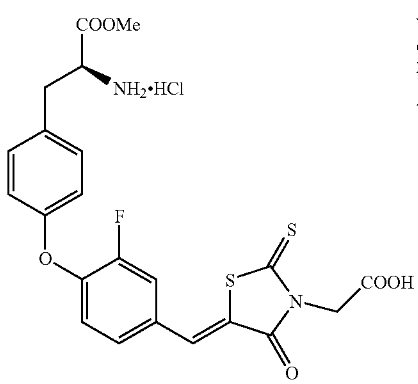 | Yield: 0.25gm(85.0%), $^1$HNMR (DMSO-$d_6$ 400MHz): δ 3.1(d, 2H), 3.7(s, 3H), 4.7(d, 2H), 7.2(t, 1H), 7.3(d, 2H), 7.5(d, 1H), 7.7(d, 1H), 7.9(s, 1H), m/z$^{m+1}$: 491.1 |
| 40 | 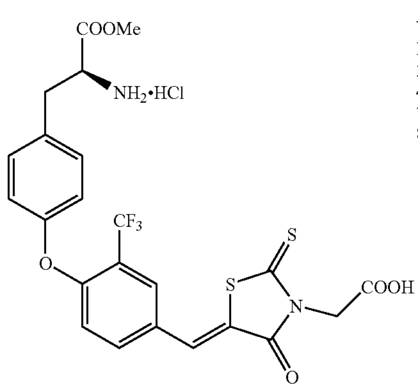 | Yield: 0.109gm(70.8%), $^1$HNMR DMSO-$d_6$ 400MHz): δ 3.1(m, 2H), 3.7(s, 3H), 4.3(t, 1H), 4.7(s, 2H), 7.0(d, 1H), 7.1(m, 2H), 7.3(dd, 2H), 7.9(d, 1H), 8.0(s, 1H), 8.1(d, 1H), m/z$^{m+1}$: 541.3. |

TABLE 5-continued
Non-reduced Rhodanine acetic acid compounds
| Example No. | Structure | Analytical Data |
|---|---|---|
| 41 | 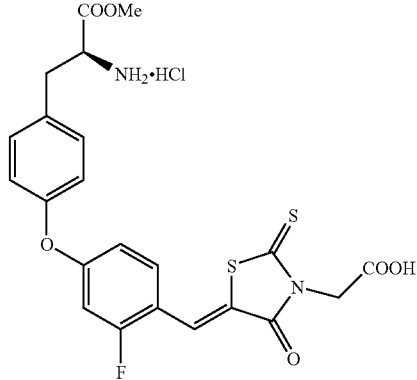 | Yield 0.4g(54.9%, HPLC Purity 97.6%); $^1$HNMR(DMSO-$d_6$ 400MHz); δ 3.1(d, 2H), 3.7(s, 3H), 4.3 (m, 1H), 4.7(s, 2H), 6.9(d, 1H), 7.0(m, 1H), 7.1(d, 2H), 7.2(d, 2H), 7.3(m, 1H), 7.6(m, 1H); m/z$^{m+1}$; 491.1 |
| 42 | 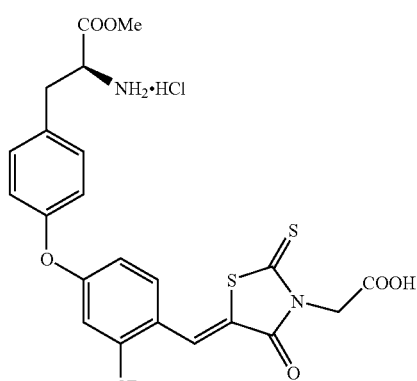 | Yield 0.100g(54.9%, HPLC Purity 97.6%); $^1$HNMR(DMSO-$d_6$ 400MHz); δ 3.1(m, 2H), 3.6(s, 3H), 4.2 (m, 1H), 4.7(s, 2H), 7.2(d, 2H), 7.3(m, 3H), 7.4(s, 1H), 7.7(d, 1H), 7.8(s, 1H); m/z$^{m+1}$; 541.2 |
| 43 | 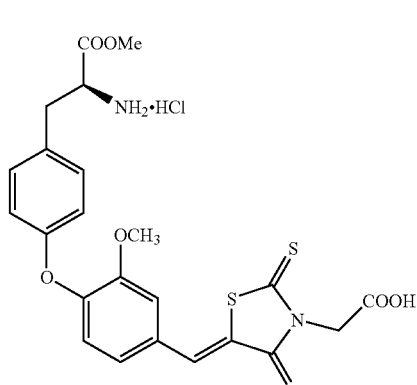 | Yield 0.124g(62.0%, HPLC Purity 95.25%); $^1$HNMR(DMSO-$d_6$, 400MHz); δ 3.1(d,2H), 3.7(s, 3H), 3.8(s, 3H), 4.3(t, 1H), 4.7(s, 2H), 6.9(d, 2H), 7.0(d, 1H), 7.2(m, 3H), 7.5(s, 1H), 7.9(s, 1H), 8.2 (bs, 2H); m/z$^{m+1}$; 502 |

TABLE 6

Reduced Rhodanine acetic acid compounds

| Example No. | Structure | Analytical Data |
|---|---|---|
| 44 | [structure] | Yield 0.095g(7%); $^1$HNMR (DMSO-$d_6$, 400MHz) δ ppm: 3.0 (2H, d), δ 3.1(1H, d), δ 3.4(2H, d), 3.6(3H, s), 4.0(1H, s), 4.2(1H, s), 6.9(4H, m), 7.21(2H, m), 7.26(2H, m). m/z$^{m+1}$: 475.1 |
| 45 | [structure] | Yield: 0.1gm(55.2%, $^1$HNMR DMSO-$d_6$ 400MHz) δ 3.1(m, 3H), 3.4(m, 1H), 3.7(s, 3H), 4.3(m, 1H), 4.5(s, 2H), 5.1(m, 1H), 6.9(m, 4H), 7.2(m, 4H), m/z$^{m+1}$: 474.8, MP-99-112° C. |
| 46 | [structure] | Yield: 0.517g(81.60%, $^1$HNMR DMSO-$d_6$ 400MHz): δ 3.13(m, 2H), 3.16(m, 1H), 3.32(d, 1H), 3.60(m, 1H), 3.7(s, 3H), 4.33(m, 1H), 4.6(s, 2H), 7.09(m, 2H), 7.24(m, 1H), 7.29(m, 3H), 7.58(d, 1H), 8.5(bs, 2H), m/z$^{m+1}$: 543.2 |

EXAMPLE 47

Lowering of Blood Glucose in Streptozotocin-induced Diabetic Mice

To induce diabetes six week old male normal Swiss Webster (SW) mice (n=6), they were given streptozotocin at a dose of 150 mg/kg body weight (ip) and after five days, when their blood glucose levels (around 350 mg/dl) they were orally gavaged with compound 2 (100 and 200 mg/kg) for next 15 days and blood glucose was monitored in every three days. The results are shown in FIG. 1.

EXAMPLE 48

Lowering of Triglyceride and Cholesterol Levels in Streptozotocin-induced Mice

Figure 2A:
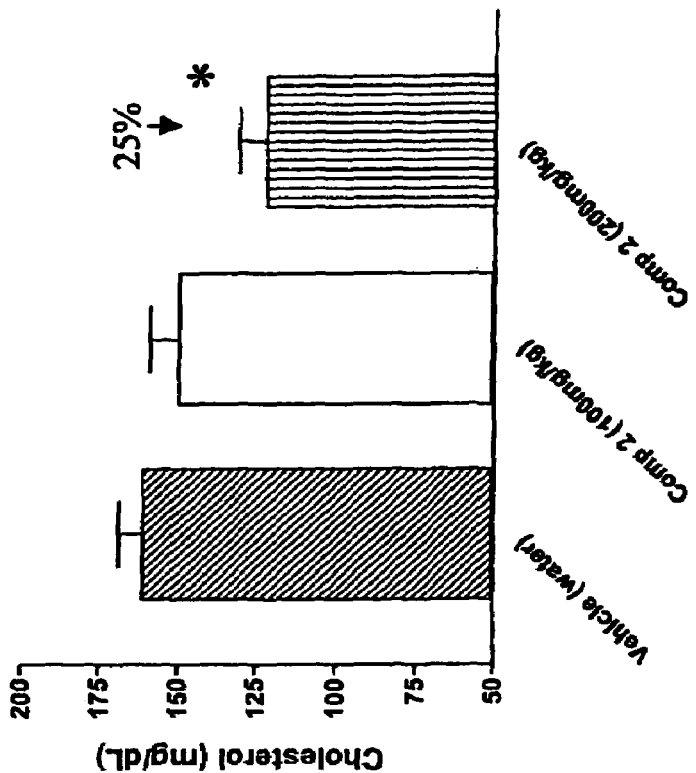
FIGS. 2A and 2B are plots of the triglyceride levels (2A) and cholesterol levels (2B) of streptozotocin-induced mice given compound 2 as described in Example 48.
Figure 2B:
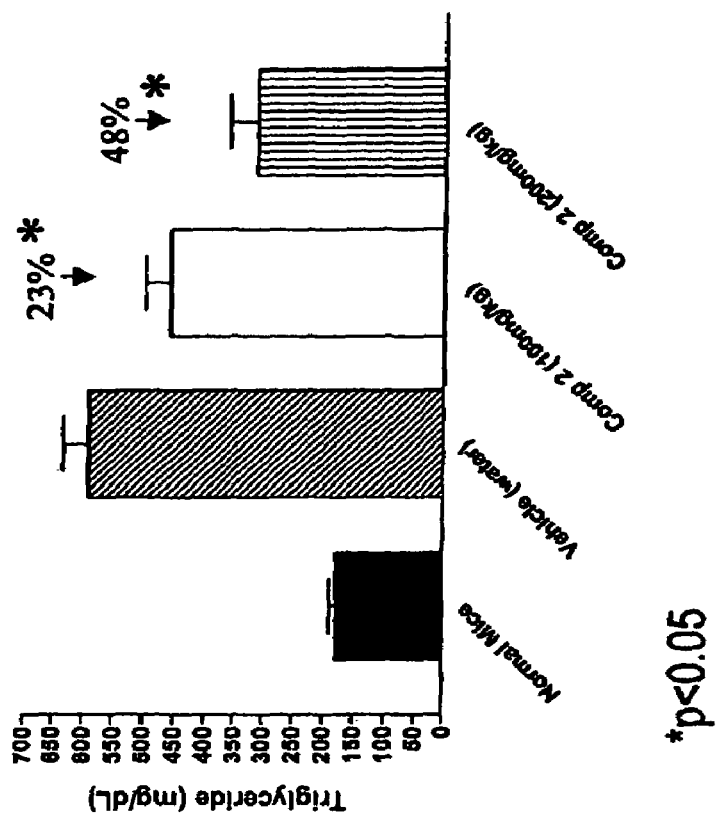

To induce diabetes in male normal SW mice (6 weeks old, n=6), they were given streptozotocin at a dose of 150 mg/kg body weight (ip) and after five days they were orally gavaged compound 2 (100 and 200 mg/kg) for 15 days. On day 15$^{th}$ serum triglycerides (A) were measured colorimetrically at 540 n-M by GPO-Trinder method, Procedure No. 339) Sigma Chemicals Inc. Similarly total plasma cholesterol was measured by Sigma procedure No. 352 using a colorimetric kit and absorbance was checked at 500 nM. The triglyceride and cholesterol levels are shown in FIGS. 2A and 2B, respectively.

EXAMPLE 49

Lowering of Blood Glucose in Non-Obese Diabetic (NOD) Mice

Figure 3:
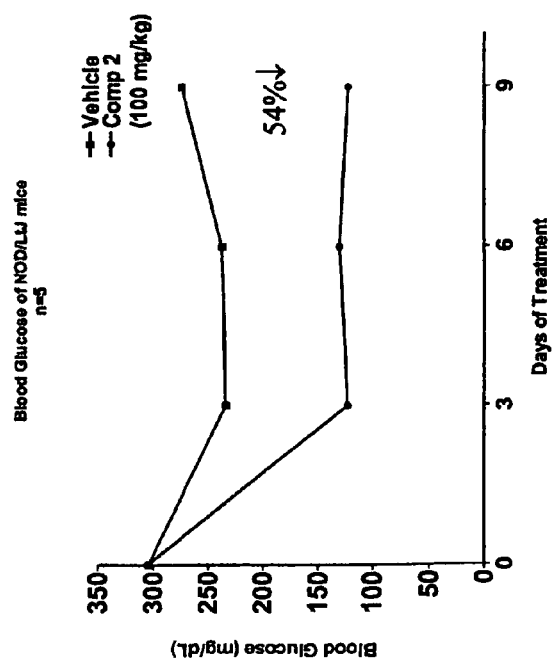
FIG. 3 is a plot of blood glucose levels of mice given compound 2 as described in Example 49.

Non-obese diabetic (NOD) mice are typical model of Type-I diabetes, where there is no circulating insulin and they eventually die because of very high blood glucose levels. When their blood glucose levels were 300 mg/dL, they were treated with compound 2 (100 mg/kg) for next 9 days and blood glucose was monitored every third day. In this experiment, compound 2 reduced the blood glucose levels in these animals. The results are shown in FIG. 3.

EXAMPLE 50

Effect of Compound 2 on Serum Glycerides, Insulin and Pancreatic Islets in NOD Mice Non-obese diabetic (NOD) mice are typical model of Type-I diabetes, where there is no circulating insulin and they eventually die because of very high blood glucose levels. When their blood glucose levels were 300 mg/dL, they were treated with compound 2 (100 mg/kg) for next 9 days and on day. 9 plasma triglyceride levels (A) were measured by mouse Insulin ELISA assay kit from ALPCO Diagnostics, NH. Pancreatic sections were made in IDEXX laboratory and no. islets were counted (C) under the microscope.

The results are shown in FIGS. 4A, 4B and 4C.

EXAMPLE 51

Figure 5B:
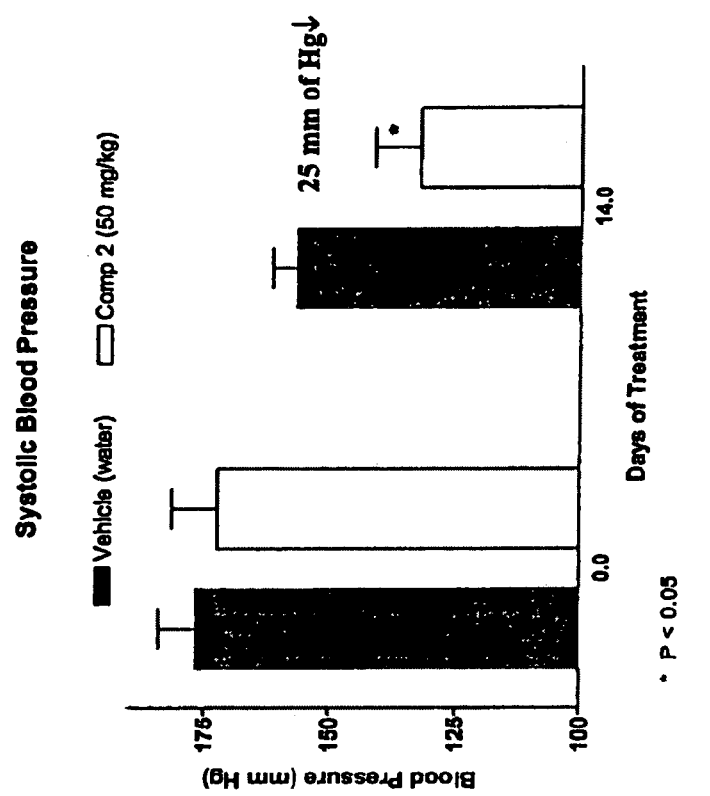
FIGS. 5A and 5B are bar graphs showing the triglyceride level and blood pressure in rats given compound 2 as described in Example 51.
Figure 5A:
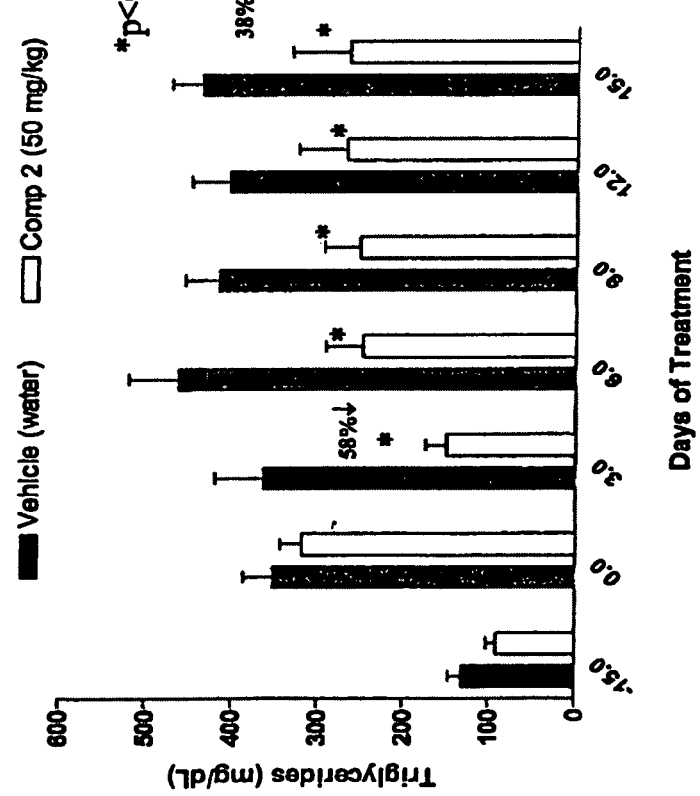

Effect of Compound 2 on Triglyceride Level and Blood Pressure in Fructose-fed Rats High fructose diet causes insulin resistance, hypertriglyceridemia and hyperinsulinemia in normal rats. Insulin resistance is a central pathophysiological feature of non-insulin dependent diabetes (NIDDM), obesity, hypertension, dyslipidemia, and atherosclerosis (collectively called Syndrome-X). Male SD rats were fed with High Fructose diet (60%) for first fifteen days without treatment. After 15 days of fructose diet their plasma triglycerides and blood pressure went high and at that time one group of animals were treated with compound-2 (50 mg/kg) for next 15 days. Blood triglycerides (FIG. 5A) were measured by GPO-Trinder method (Sigma) every three days and Blood pressure (FIG. 5B) was monitored by XBP 1000 rat tail blood pressure system, Kent scientific Inc. Compound 2 decreases both TG and blood pressure in this model.

EXAMPLE 52

Compound 2 is not an Agonist of PPARα, γ and δ

Figure 6:
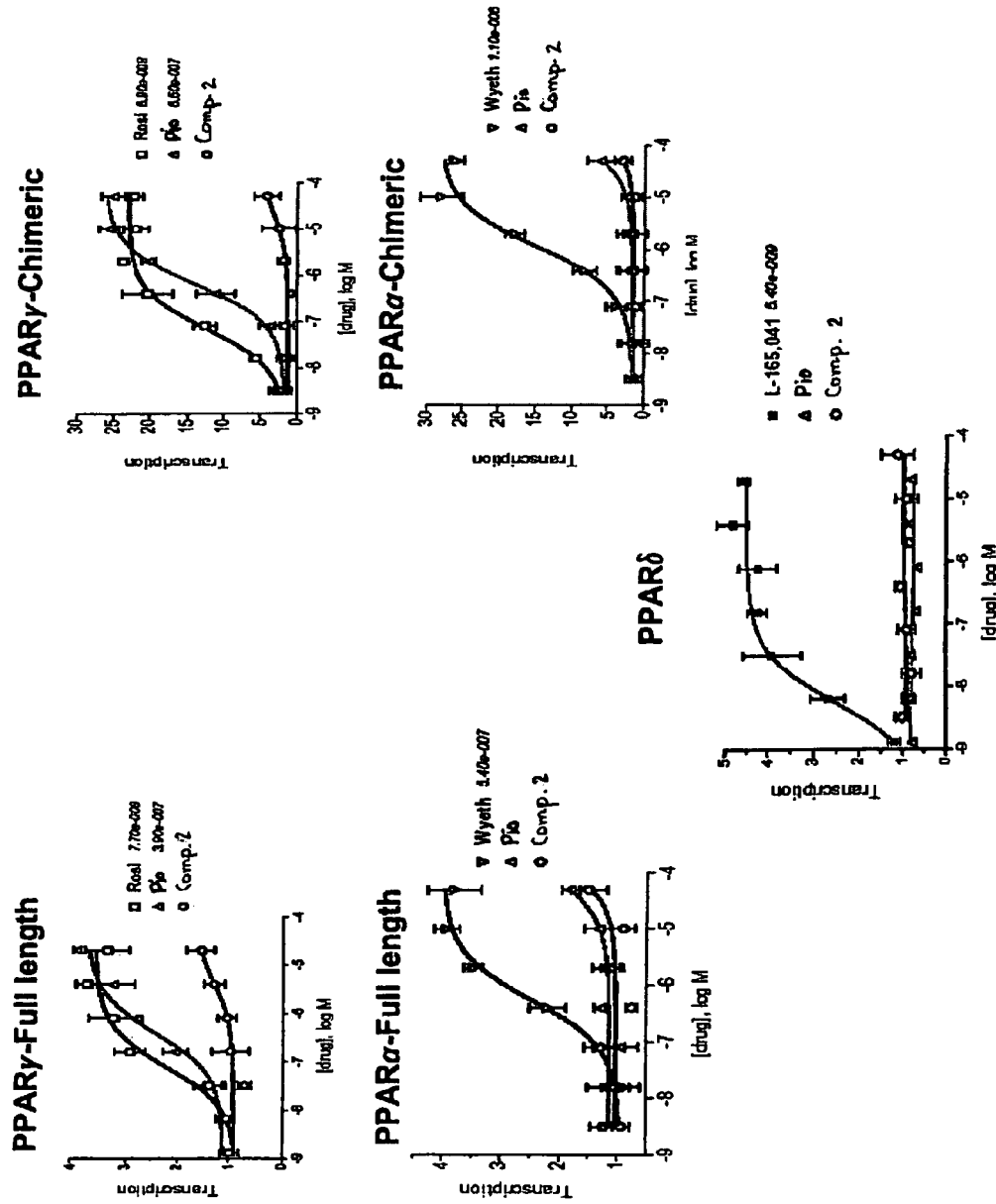
FIG. 6 is a series of plots of the transcription of PPARα, PPAR-γ (full length and chimeric) and PPARδ in NIH 3T3 cells activated with Rosiglitazone, Pioglitazone, compound 2, or other controls as described in Example 52.

A transactivation experiment was carried out in NIH 3T3 cells with either the full length or chimeric PPARγ gene and FATP-PPRE reporter construct. Rosiglitazone (Rosi) and Pioglitazone (Pio) were kept as positive controls. Compared to rosiglitazone and pioglitazone, compound 2 did not show any PPAR-γ affinity in this system. A transactivation experiment was carried out in NIH 3T3 cells with the full length or chimeric PPARα gene and FATP-PPRE reporter construct. Wyl4643 (Wyeth) was kept as positive control. Compared to that, compound 2 did not show any PPARα affinity in this system. A transactivation experiment was carried out in NIH 3T3 cells with the full length PPARδ gene and FATP-PPRE reporter construct. L165041 (L-165) was kept as positive control. The results are shown in FIG. 6.

EXAMPLE 53

Efficacy In Vitro of Compounds 2 and 16

Figure 7:
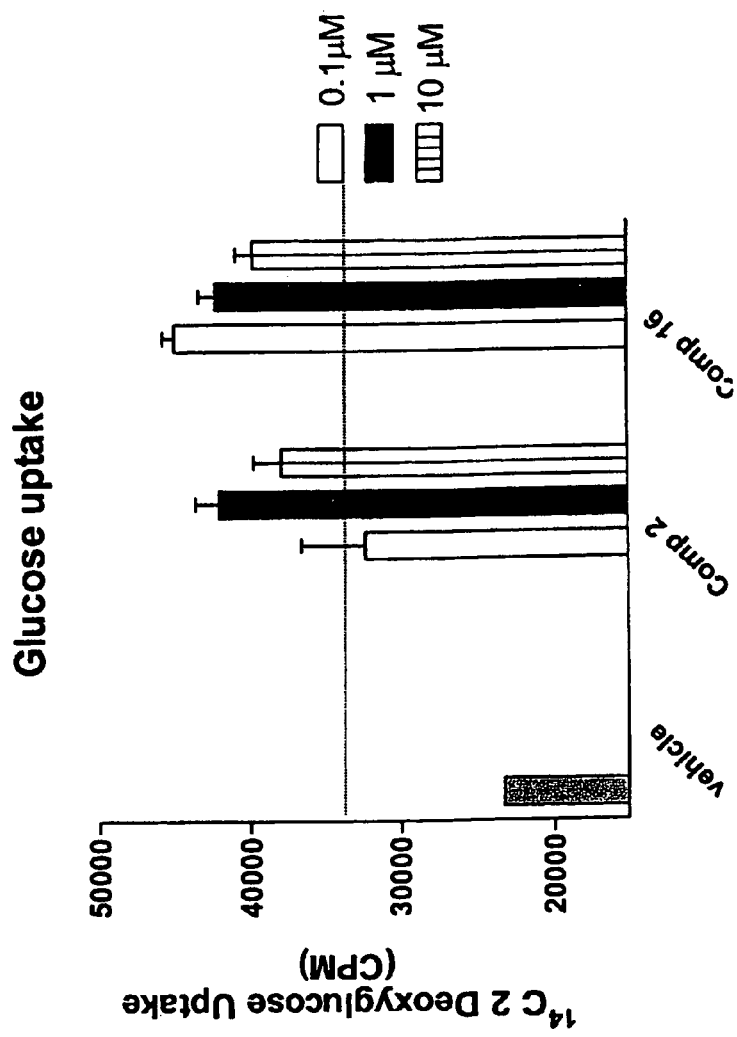
FIG. 7 is a bar graph of the glucose uptake of adipocytes treated with compounds 2 or 16 at concentrations of 0.1, 1, and 10 μM as described in Example 53.

3T3-L1 fibroblasts were differentiated to adipocytes by a cocktail containing insulin, dexamethasone and IBMX for several days. Fully differentiated adipocytes were treated with the compounds (2 and 16 at 0.1, 1, and 10 uM concentrations) or 0.1% DMSO for 72 hrs and then glucose uptake was carried out for 15 min without any insulin. Basal uptake was initiated by addition of radioactive 14C-2DOG and after 15 min they were washed with cold PBS with cold glucose. The results are shown in FIG. 7.

EXAMPLE 54

Efficacy In Vitro of Compound 16 in db/db Mice

Figure 8:
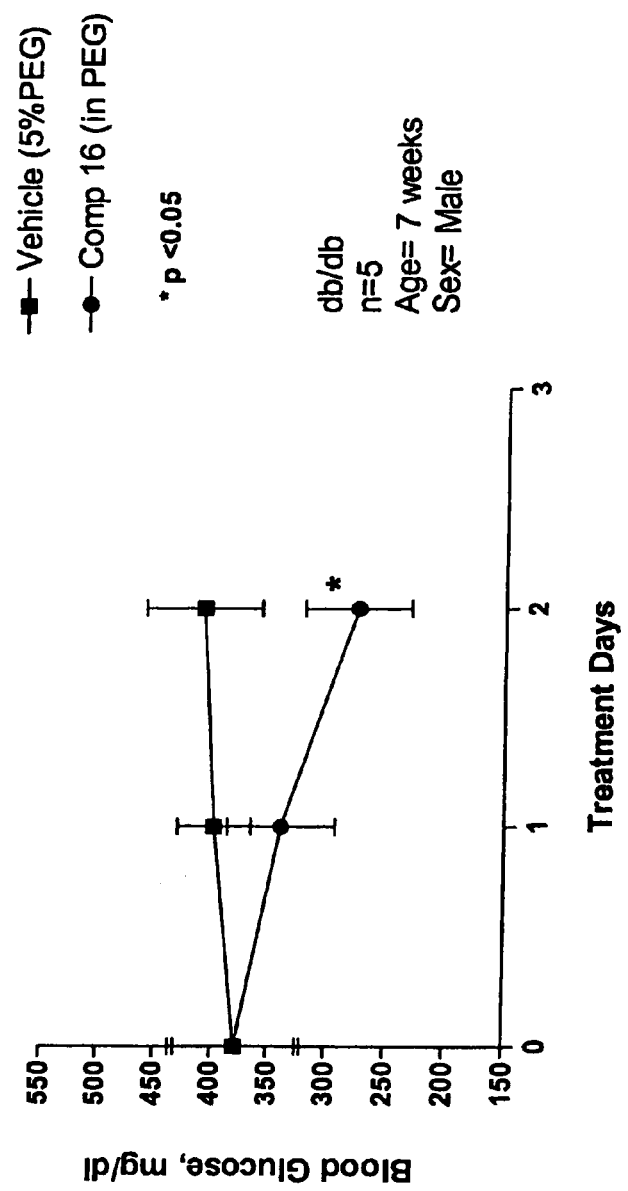
FIG. 8 is a plot of blood glucose levels in mice treated with compound 16 as described in Example 54.

Seven weeks old male db/db (spontaneous model) diabetic mice were orally treated with compound 16 at a dose of 50 mg/kg body weight in 5% PEG and blood glucose was monitored by one touch glucometer. This compound is not water soluble so PEG is used as vehicle. The results are shown in FIG. 8.

EXAMPLE 55

Compounds 2 and 16 are not Adipogenic

Figure 9:
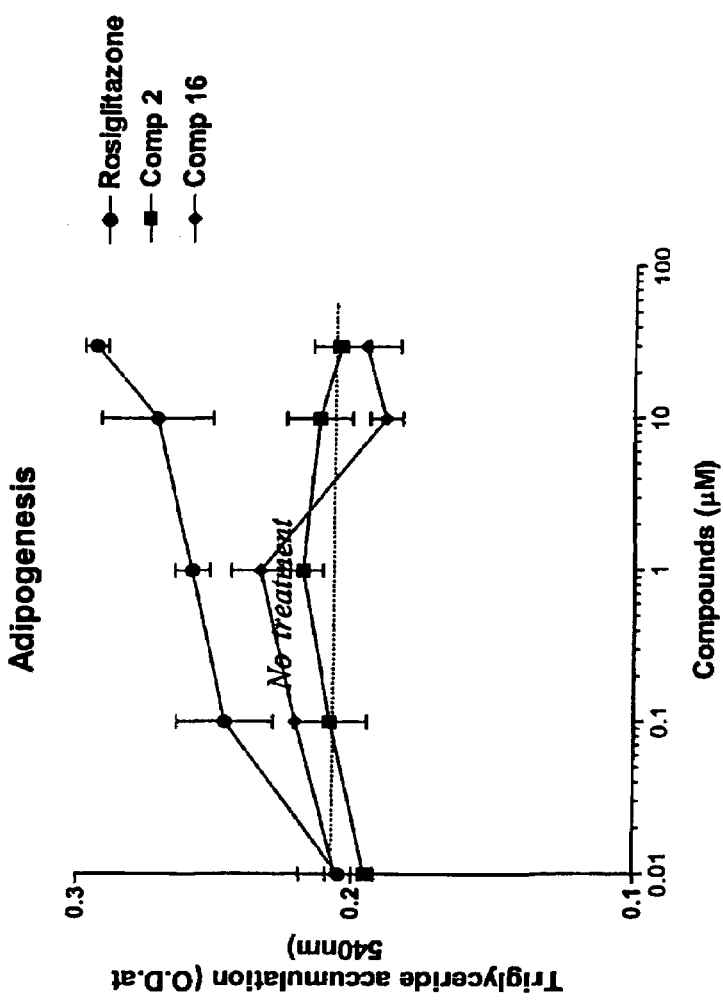
FIG. 9 is a plot of the triglyceride accumulation by adipogenesis assay on fibroblasts treated with compounds 2 and 16 as described in Example 55.

Although it was shown that compound 2 does not induce adipogenesis or aP2 expression like other known or PPARγ agonists, a test was performed to see the effect of its acid form in similar adipogenesis experiments in 3T3-L1 fibroblasts. All known PPAR-g agonists induce differentiation in fibroblast cells. The adipogenic potential of these compounds are correlated with their affinity to this receptor. To check quickly whether compound 2, compound 16 have any affinity to this receptors, 3T3-L1 fibroblasts were treated with either DMSO control or rosiglitazone as positive control or these two compounds for several days at different concentrations. On day 11$^{th}$, the differentiated adipocytes were stained with Oil-red-O (Sigma) and washed thoroughly to remove unbound stain. The red cooler was extracted with isopropanol and measured calorimetrically at 540 nM. PPAR-g agonist rosiglitazone strongly induced adipogenesis in this cell system whereas both compound 2 and 16 remained unchanged, this is the indirect proof that not only compound 2 but also compound 16 has no affinity to PPARg receptor. The results are shown in FIG. 9.

EXAMPLE 56

Lowering of Blood Glucose by Compounds 20 and 36 in db/db Mice

Figure 10:
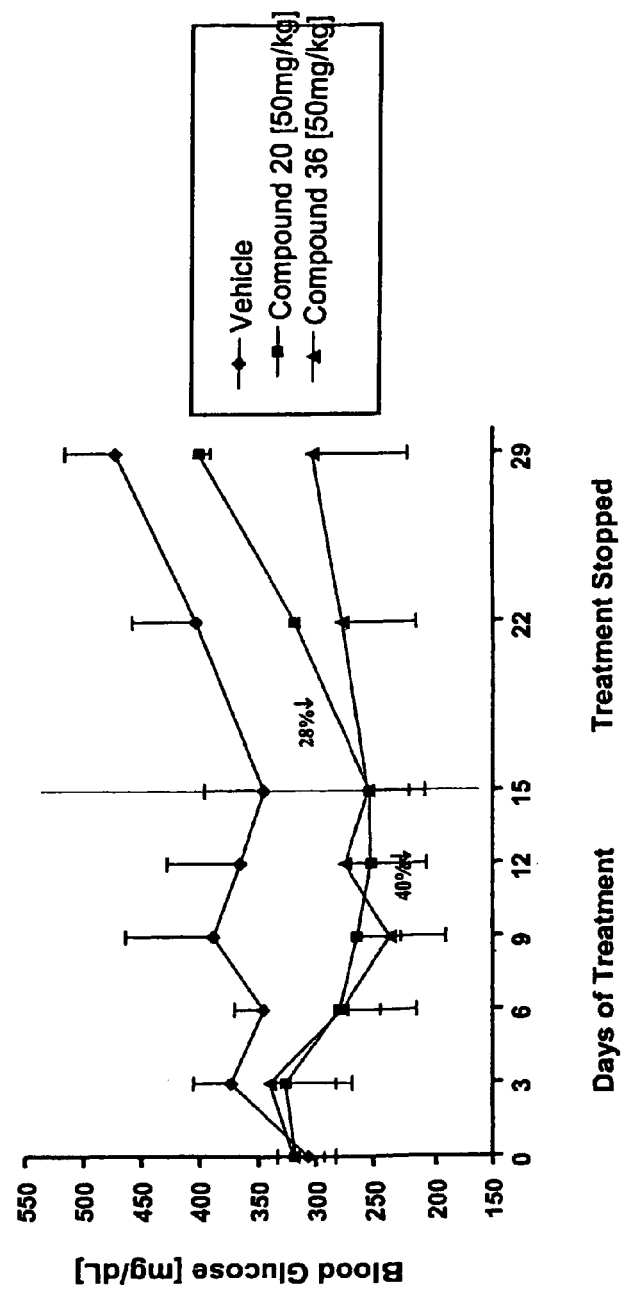
FIG. 10 is a plot of blood glucose levels in mice treated with compounds 20 and 36 as described in Example 56.

Seven weeks old male db/db (spontaneous model) diabetic mice were orally treated with compound 20 and 36, at a dose of 50 mg/kg body weight in 5% PEG and blood glucose was monitored by one touch glucometer. Both the compound show glucose lowering activity in this animal model of Type-II diabetes. The results are shown in FIG. 10.

EXAMPLE 57

Figure 11A:
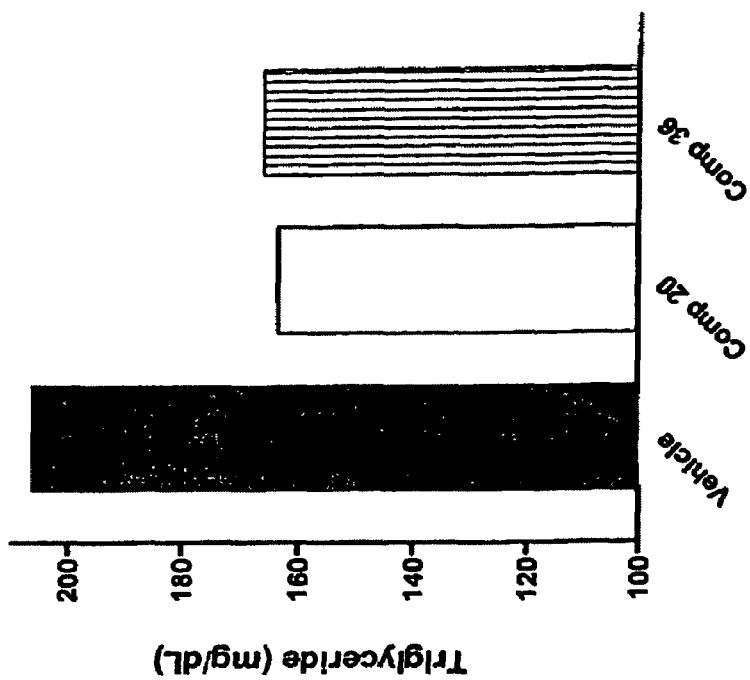
FIGS. 11A and 11B are plots of body weight change and triglyceride level in mice treated with compounds 20 and 36 as described in Example 57.
Figure 11B:
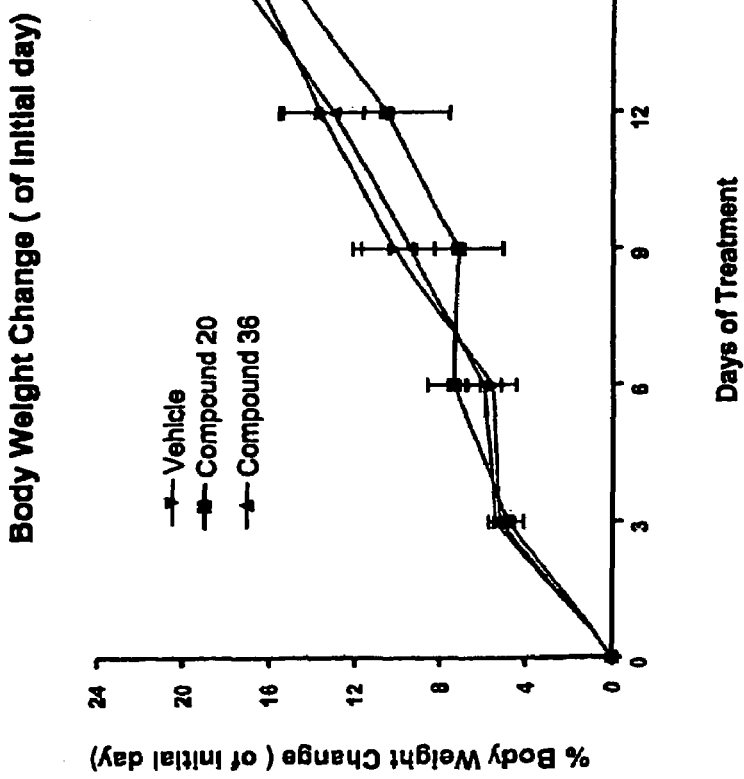

Effect of Compounds 20 and 36 on Body Weight and Triglyceride Levels in db/db Mice Seven weeks old male db/db (spontaneous model) diabetic mice were orally treated with compound 20 and 36, at a dose of 50 mg/kg body weight in 5% PEG and blood glucose was monitored by one touch glucometer. Both the compounds show control of bodyweight and decrease of plasma triglyceride levels compare to untreated controls. The results are shown in FIGS. 11A and 11B.

EXAMPLE 58

Lowering of Blood Glucose in ob/ob Mice by Compound 36

Figure 12A:
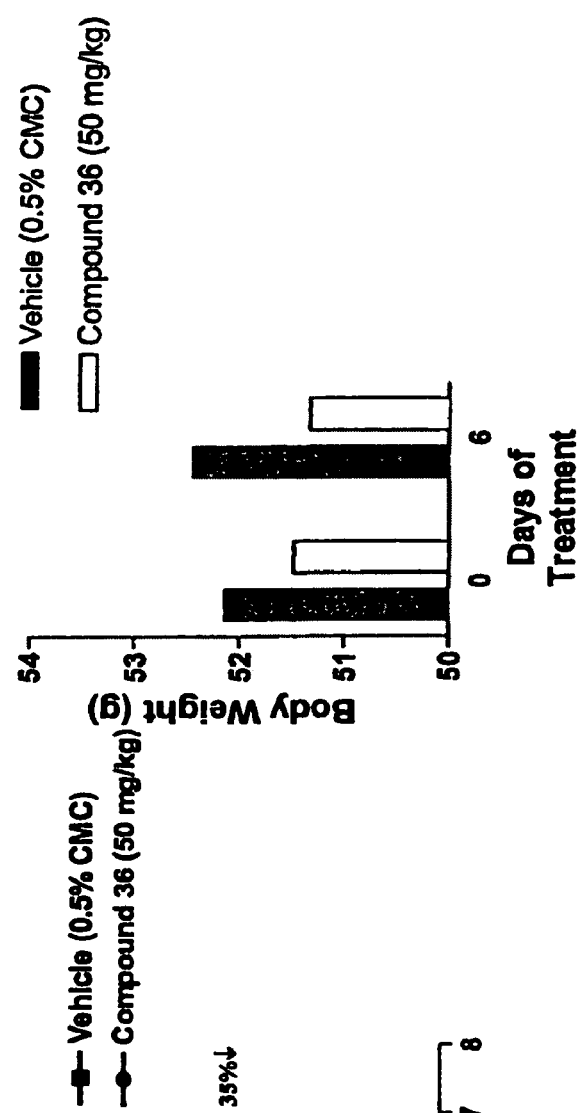
FIGS. 12A and 12B are graphs of blood glucose levels and body weight in mice treated with compound 36 as described in Example 58.
Figure 12B:
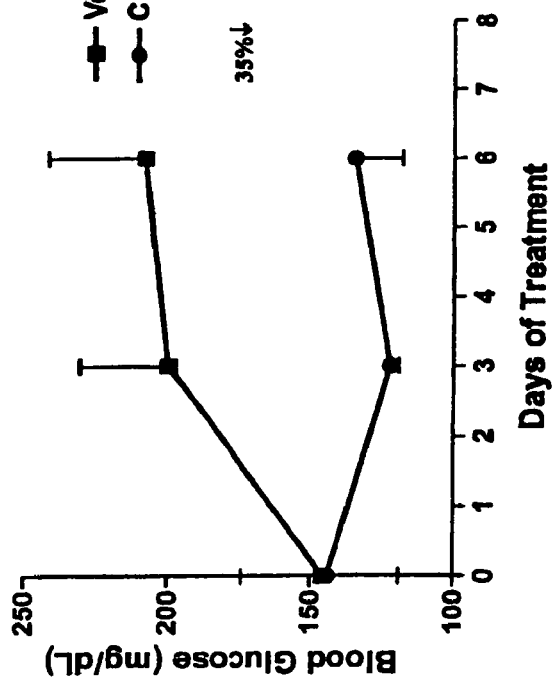

Seven weeks old male ob/ob (Obese, insulin resistant spontaneous model of Type-II diabetes) diabetic mice were orally treated with compound 36, at a dose of 50 mg/kg body weight in 5% PEG and blood glucose (FIG. 12A) was monitored by one touch glucometer on day 3 and day 6. Compound 36 show strong glucose lowering (A) activity in this animal model of Type-II diabetes. Body weight (FIG. 12B) was also not increased after the treatment of compound 36 compare to controls.

EXAMPLE 59

Inhibition of Aldose Reductase by Compounds 2 and 16

Aldose reductase, a member of the monomer NADPH-dependent aldo-ketreductase, is a rate-limiting enzyme in the polyol pathway which catalyzes the reduction of various aldehydes. This includes reduction of the aldehyde form of glucose to its corresponding sugar alcohol sorbitol. Accumulation of sorbitol has been reported in the lens, nerve, kidney and retina of diabetic animals. Large amounts of sorbitol causes osmotic disruption which may be one of the etiologic factors in the pathogenesis of some diabetic complications like retinopathy, neuropathy, nephropathy and atherosclerosis.

Figure 13B:
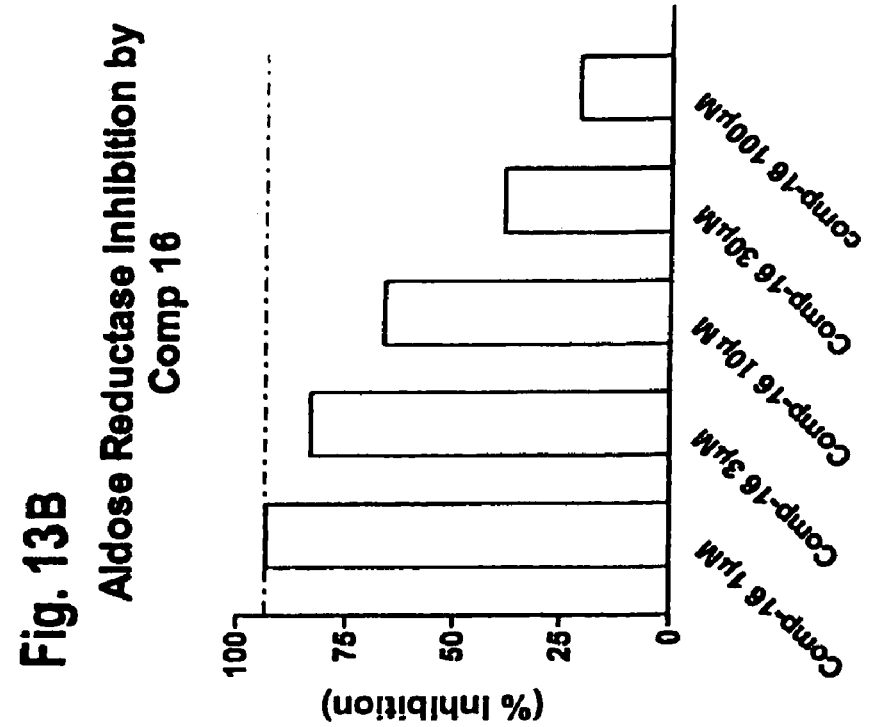
FIGS. 13A and 13B are bar graphs of aldose reductase inhibition by compound 2 (FIG. 13A) and compound 16 (FIG. 13B) as described in Example 59.
Figure 13A:
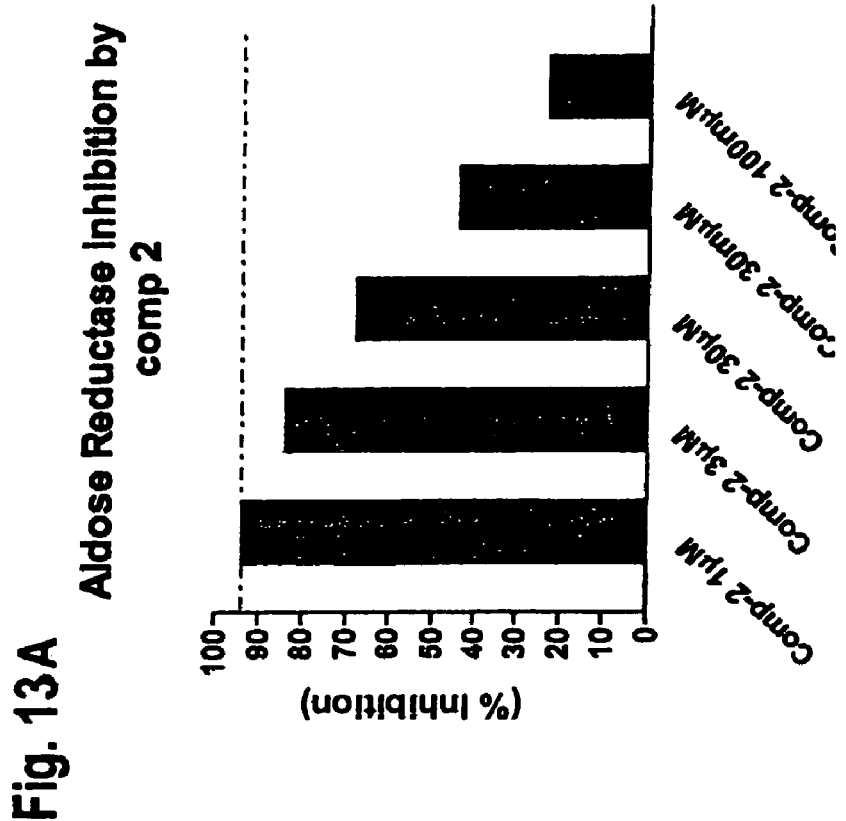

Aldose reductase from rat lens partially purified by tissue homogenization is used. Test compound and/or vehicle, 0.6 mg enzyme, 0.2 mM NADPH and phosphate assay buffer pH 6.2 are preincubated at 25° C. for 3 minutes. Absorbance is observed at 340 nm for the initial zero time value. The reaction is then initiated by addition of 10 mM DL-glyceraldehyde and incubation is continued for 20 minutes at 25° C. at which time the final absorbance is noted. Enzyme activity is determined by the difference between the initial and final absorbance. The results are shown in FIGS. 13A and 13B.

The invention claimed is:

1. Diphenyl ether compounds of the formula (I)

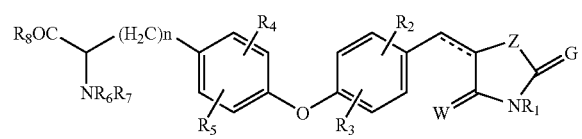

(I)

their tautomeric forms, their stereoisomers, their pharmaceutically acceptable salts, their pharmaceutically acceptable solvates, wherein ---- represents an optional bond;

W represents O or S;

Z represents O or S;

G represents O or S;

$R_1$ is selected from the group consisting of hydrogen, substituted and unsubstituted ($C_1$-$C_{20}$) alkyl, ($C_2$-$C_{20}$) alkenyl, —$CH_2COOR$, ($C_5$-$C_{14}$) aryl and a counter ion, wherein R is selected from the group consisting of H and a ($C_1$-$C_6$) alkyl;

$R_2$, $R_3$, $R_4$ and $R_5$ are independently selected from the group consisting of hydrogen, halo, hydroxyl, nitro, cyano, formyl, amino, linear and branched, substituted and unsubstituted ($C_1$-$C_{20}$) alkyl, and substituted and unsubstituted ($C_1$-$C_{20}$) alkoxy;

$R_6$ and $R_7$ are independently selected from the group consisting of H, $COR_{12}$, substituted and unsubstituted ($C_1$-$C_{20}$) alkyl, ($C_2$-$C_{20}$) alkenyl, ($C_5$-$C_{14}$) aryl, ($C_1$-$C_{13}$) heteroaryl and ($C_1$-$C_{11}$) heterocyclyl; where $R_{12}$ is selected from the group consisting of H, substituted and unsubstituted ($C_1$-$C_{20}$) alkyl, ($C_2$-$C_{20}$) alkenyl, ($C_5$-$C_{14}$) aryl, ($C_2$-$C_{20}$) alkenyloxy, ($C_5$-$C_{14}$) aryloxy, ($C_1$-$C_{20}$) alkoxy and ($C_6$-$C_{34}$) aralkoxy;

$R_8$ represents $OR_{13}$ or $NR_{14}R_{15}$; where $R_{13}$ is selected from the group consisting of hydrogen, substituted and unsubstituted ($C_1$-$C_{20}$) alkyl, ($C_2$-$C_{20}$) alkenyl, ($C_5$-$C_{14}$) aryl, ($C_6$-$C_{34}$) aralkyl, ($C_1$-$C_{13}$) heteroaryl, and a counter ion; and where $R_{14}$ and $R_{15}$ are independently selected from the group consisting of H, substituted and unsubstituted ($C_1$-$C_{20}$) alkyl, ($C_2$-$C_{20}$) alkenyl and ($C_5$-$C_{14}$) aryl; and n=1.

2. A compound according to claim 1 wherein the ---- represents a bond.

3. A compound according to claim 1 wherein the ---- is absent.

4. A compound according to claim 2 wherein W and G represent O; Z represents S; $R_{13}$ is selected from the group consisting of H, substituted and unsubstituted ($C_1$-$C_6$) alkyl and a counterion; and $R_{14}$ and $R_{15}$ are independently selected from the group consisting of substituted and unsubstituted ($C_1$-$C_6$) alkyl.

5. A compound according to claim 4 wherein $R_2$ and $R_3$ are independently selected from the group consisting of H, halo, nitro, substituted and unsubstituted ($C_1$-$C_6$) alkyl and substituted and unsubstituted ($C_1$-$C_6$) alkoxy.

6. A compound according to claim 3 wherein W and G represent O; Z represents S; $R_{13}$ is selected from the group consisting of H, substituted and unsubstituted ($C_1$-$C_6$) alkyl and a counterion; and $R_{14}$ and $R_{15}$ are independently selected from the group consisting of substituted and unsubstituted ($C_1$-$C_6$) alkyl.

7. A compound according to claim 6 wherein $R_2$ and $R_3$ are independently selected from the group consisting of H, halo, substituted and unsubstituted ($C_1$-$C_6$) alkyl and substituted and unsubstituted ($C_1$-$C_6$) alkoxy.

8. A compound according to claim 2 wherein W represents O; G and Z represent S; and $R_{13}$ is selected from the group consisting of substituted and unsubstituted ($C_1$-$C_6$) alkyl.

9. A compound according to claim 8 wherein $R_2$ and $R_3$ are independently selected from the group consisting of H, halo, substituted and unsubstituted ($C_1$-$C_6$) alkyl and substituted and unsubstituted ($C_1$-$C_6$) alkoxy.

10. A compound according to claim 3 wherein W represents O; G and Z represent S;

and $R_{13}$ is selected from the group consisting of substituted and unsubstituted ($C_1$-$C_6$) alkyl.

11. A compound according to claim 10 wherein $R_2$ and $R_3$ are independently selected from the group consisting of H, halo, substituted and unsubstituted ($C_1$-$C_6$) alkyl and substituted and unsubstituted ($C_1$-$C_6$) alkoxy.

12. A compound according to claim 2 wherein W represents O; G and Z represent S; and $R_{13}$ is selected from the group consisting of substituted and unsubstituted $(C_1-C_6)$ alkyl; and $R_1$ represents —$CH_2COOR$.

13. A compound according to claim 12 wherein $R_2$ and $R_3$ are independently selected from the group consisting of H, halo, substituted and unsubstituted $(C_1-C_6)$ alkyl and substituted and unsubstituted $(C_1-C_6)$ alkoxy.

14. A compound according to claim 3 wherein W represents O; G and Z represent S; and $R_{13}$ is selected from the group consisting of substituted and unsubstituted $(C_1-C_6)$ alkyl; and $R_1$ represents —$CH_2COOR$.

15. A compound according to claim 14 wherein $R_2$ and $R_3$ are independently selected from the group consisting of H and substituted and unsubstituted $(C_1-C_6)$ alkyl.

16. A compound according to claim 4 selected from the group consisting of
- (S)-2=Amino-3-{4-[4-(2,4-dioxo-thiazolidin-5-ylidenemethyl)-phenoxy]-phenyl}-propionic acid methyl ester hydrochloric acid salt
- (S)-2-Amino-3-{4-[4-(2,4-dioxo-thiazolidin-5-ylmethyl)-phenoxy]-phenyl}-propionic acid methyl ester hydrochloric acid salt
- (S)-2-Amino-3-{4-[4-(2,4-dioxo-thiazolidin-5-ylidenemethyl)-3-fluoro-phenoxy]-phenyl}-propionic acid methyl ester hydrochloric acid salt
- (S)-2-Amino-3-{4-[2-chloro-4-(2,4-dioxo-thiazolidin-5-ylidenemethyl)-phenoxy]-phenyl}-propionic acid methyl ester hydrochloric acid salt
- (S)-2-Amino-3-{4-[4-(2,4-dioxo-thiazolidin-5-ylidenemethyl)-2-methoxy-phenoxy]-phenyl}-propionic acid methyl ester hydrochloric acid salt
- (S)-2-Amino-3-{4-[4-(2,4-dioxo-thiazolidin-5-ylidenemethyl)-2-nitro-phenoxy]-phenyl}-propionic acid methyl ester hydrochloric acid salt
- (S)-2-Amino-3-{4-[4-(2,4-dioxo-thiazolidin-5-ylidenemethyl)-3-trifluoromethyl-phenoxy]-phenyl}-propionic acid methyl ester hydrochloric acid salt
- (S)-2-Amino-3-{4-[4-(2,4-dioxo-thiazolidin-5-ylidenemethyl)-phenoxy]-phenyl}-propionic acid
- (S)-2-Amino-3-{4-[4-(2,4-dioxo-thiazolidin-5-ylidenemethyl)-phenoxy]-phenyl}-propionate dipotassium salt
- (S)-2-Amino-3-{4-[4-(2,4-dioxo-thiazolidin-5-ylidenemethyl)-phenoxy]-phenyl}-propionate disodium salt.

17. A compound according to claim 6 selected from the group consisting of
- (S)-2-Amino-3-{4-[3-chloro-4-(2,4-dioxo-thiazolidin-5-ylmethyl)-phenoxy]-phenyl}-propionic acid methyl ester hydrochloric acid salt
- (S)-2-Amino-3-{4-[2-chloro-4-(2,4-dioxo-thiazolidin-5-ylmethyl)-phenoxy]-phenyl}-propionic acid methyl ester hydrochloric acid salt
- (S)-2-Amino-3-{4-[4-(2,4-dioxo-thiazolidin-5-ylmethyl)-2-methoxy-phenoxy]-phenyl}-propionic acid methyl ester hydrochloric acid salt
- (S)-2-Amino-3-{4-[4-(2,4-dioxo-thiazolidin-5-ylmethyl)-2-fluoro-phenoxy]-phenyl}-propionic acid methyl ester hydrochloric acid salt
- (S)-2-Amino-3-{4-[4-(2,4-dioxo-thiazolidin-5-ylmethyl)-phenoxy]-phenyl}-propionic acid hydrochloric acid salt
- (S)-2-Amino-3-{4-[4-(2,4-dioxo-thiazolidin-5-ylmethyl)-phenoxy]-phenyl}-propionate disodium salt
- (S)-2-Amino-3-{4-[4-(2,4-dioxo-thiazolidin-5-ylmethyl)-phenoxy]-phenyl}-propionate dipotassium salt
- (S)-2-Amino-3-{4-[4-(2,4-dioxo-thiazolidin-5-ylmethyl)-phenoxy]-phenyl}-N,N-dimethyl-propionamide hydrochloric acid salt.

18. A compound according to claim 8 selected from the group consisting of
- (R,S)-2-Amino-3-{4-[4-(4-oxo-2-thioxo-thiazolidin-5-ylidenemethyl)-phenoxy]-phenyl}-propionic acid methyl ester hydrochloric acid salt
- (S)-2-Amino-3-{4-[3-fluoro-4-(4-oxo-2-thioxo-thiazolidin-5-ylidenemethyl)-phenoxy]-phenyl}-propionic acid methyl ester hydrochloric acid salt
- (S)-2-Amino-3-{4-[2-fluoro-4-(4-oxo-2-thioxo-thiazolidin-5-ylidenemethyl)-phenoxy]-phenyl}-propionic acid methyl ester hydrochloric acid salt
- (S)-2-Amino-3-{4-[3-chloro-4-(4-oxo-2-thioxo-thiazolidin-5-ylidenemethyl)-phenoxy]-phenyl}-propionic acid methyl ester hydrochloric acid salt
- (S)-2-Amino-3-{4-[2-chloro-4-(4-oxo-2-thioxo-thiazolidin-5-ylidenemethyl)-phenoxy]-phenyl}-propionic acid methyl ester hydrochloric acid salt
- (S)-2-Amino-3-{4-[2-methoxy-4-(4-oxo-2-thioxo-thiazolidin-5-ylidenemethyl)-phenoxy]-phenyl}-propionic acid methyl ester hydrochloric acid salt
- (S)-2-Amino-3-{4-[4-(4-oxo-2-thioxo-thiazolidin-5-ylidenemethyl)-phenoxy]-phenyl}-propionic acid methyl ester
- (S)-2-Amino-3-{4-[4-(4-oxo-2-thioxo-thiazolidin-5-ylidenemethyl)-2-trifluoromethyl-phenoxy]-phenyl}-propionic acid methyl ester hydrochloric acid salt
- (S)-2-Amino-3-{4-[4-(4-oxo-2-thioxo-thiazolidin-5-ylidenemethyl)-3-trifluoromethyl-phenoxy]-phenyl}-propionic acid methyl ester hydrochloric acid salt.

19. A compound according to claim 10 selected form the group consisting of
- (S)-2-Amino-3-{4-[2-methoxy-4-(4-oxo-2-thioxo-thiazolidin-5-ylmethyl)-phenoxy]-phenyl}-propionic acid methyl ester hydrochloric acid salt
- (R,S)-2-Amino-3-{4-[4-(4-oxo-2-thioxo-thiazolidin-5-ylmethyl)-phenoxy]-phenyl}-propionic acid methyl ester
- (S)-2-Amino-3-{4-[2-chloro-4-(4-oxo-2-thioxo-thiazolidin-5-ylmethyl)-phenoxy]-phenyl}-propionic acid methyl ester hydrochloric acid salt
- (S)-2-Amino-3-{4-[3-chloro-4-(4-oxo-2-thioxo-thiazolidin-5-ylmethyl)-phenoxy]-phenyl}-propionic acid methyl ester hydrochloric acid salt
- (S)-2-Amino-3-{4-[3-fluoro-4-(4-oxo-2-thioxo-thiazolidin-5-ylmethyl)-phenoxy]-phenyl}-propionic acid methyl ester hydrochloric acid salt
- (S)-2-Amino-3-{4-[2-fluoro-4-(4-oxo-2-thioxo-thiazolidin-5-ylmethyl)-phenoxy]-phenyl}-propionic acid methyl ester hydrochloric acid salt
- (S)-2-Amino-3-{4-[4-(4-oxo-2-thioxo-thiazolidin-5-ylmethyl)-3-trifluoromethyl-phenoxy]-phenyl}-propionic acid methyl ester hydrochloric acid salt.

20. A compound according to claim 12 selected from the group consisting of
- (R,S)-2-Amino-3-{4-[4-(3-carboxymethyl-4-oxo-2-thioxo-thiazolidin-5-ylidenemethyl)-phenoxy]-phenyl}-propionic acid methyl ester hydrochloric acid salt
- (S)-2-Amino-3-{4-[4-(3-carboxymethyl-4-oxo-2-thioxo-thiazolidin-5-ylidenemethyl)-3-chloro-phenoxy]-phenyl}-propionic acid methyl ester hydrochloric acid salt
- (S)-2-Amino-3-{4-[4-(3-carboxymethyl-4-oxo-2-thioxo-thiazolidin-5-ylidenemethyl)-2-chloro-phenoxy]-phenyl}-propionic acid methyl ester hydrochloric acid salt
- (S)-2-Amino-3-{4-[4-(3-carboxymethyl-4-oxo-2-thioxo-thiazolidin-5-ylidenemethyl)-2-fluoro-phenoxy]-phenyl}-propionic acid methyl ester hydrochloric acid salt (S)-2-Amino-3-{4-[4-(3-carboxymethyl-4-oxo-2-thioxo-thiazolidin-5-ylidenemethyl)-2-trifluoromethyl-phenoxy]-phenyl}-propionic acid methyl ester hydrochloric acid salt (S)-2-Amino-3-{4-[4-(3-carboxymethyl-4-oxo-2-thioxo-thiazolidin-5-ylidenemethyl)-3-fluoro-phenoxy]-phenyl}-propionic acid methyl ester hydrochloric acid salt (S)-2-Amino-3-{4-[4-(3-carboxymethyl-4-oxo-2-thioxo-thiazolidin-5-ylidenemethyl)-3-trifluoromethyl-phenoxy]-phenyl}-propionic acid methyl ester hydrochloric acid salt (S)-2-Amino-3-{4-[4-(3-carboxymethyl-4-oxo-2-thioxo-thiazolidin-5-ylidenemethyl)-2-methoxy-phenoxy]-phenyl}-propionic acid methyl ester hydrochloric acid salt.

21. A compound according to claim 14 selected from the group consisting of (RS)-2-Amino-3-{4-[4-(3-carboxymethyl-4-oxo-2-thioxo-thiazolidin-5-ylmethyl)-phenoxy]-phenyl}-propionic acid methyl ester hydrochloric acid salt (S)-2-Amino-3-{4-[4-(3-carboxymethyl-4-oxo-2-thioxo-thiazolidin-5-ylmethyl)-phenoxy]-phenyl}-propionic acid methyl ester hydrochloric acid salt (S)-2-Amino-3-{4-[4-(3-carboxymethyl-4-oxo-2-thioxo-thiazolidin-5-ylmethyl)-3-trifluoromethyl-phenoxy]-phenyl}-propionic acid methyl ester hydrochloric acid salt.

22. A compound as claimed in claim 1, wherein said pharmaceutical acceptable salt is selected from the group consisting of a hydrochloride, hydrobromide, potassium and magnesium salt.

23. A pharmaceutical composition comprising a therapeutically effective amount of a compound or mixture of compounds according to any one of claims 1 to 15 and 22 and a pharmaceutically acceptable carrier sufficient to reduce in a subject the plasma level of glucose, fatty acids, cholesterol or triglycerides.

24. A pharmaceutical composition comprising a therapeutically effective amount of a compound or mixture of compounds according to any one of claims 1 to 15 and 22 and a pharmaceutically acceptable carrier sufficient to treat obesity, autoimmune diseases, inflammation, immunological diseases, diabetes or disorders associated with insulin resistance in a subject.

* * * * *